US010071252B2

(12) United States Patent
Peterson

(10) Patent No.: US 10,071,252 B2
(45) Date of Patent: Sep. 11, 2018

(54) METHODS AND SYSTEMS FOR WIRELESS COMMUNICATION WITH A SUBCUTANEOUS MEDICAL DEVICE

(71) Applicant: Valencia Technologies Corporation, Valencia, CA (US)

(72) Inventor: David K. L. Peterson, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 0 days.

(21) Appl. No.: 15/246,489

(22) Filed: Aug. 24, 2016

(65) Prior Publication Data

US 2017/0056679 A1 Mar. 2, 2017

Related U.S. Application Data

(60) Provisional application No. 62/209,875, filed on Aug. 25, 2015.

(51) Int. Cl.
*A61N 1/37* (2006.01)
*A61N 1/372* (2006.01)
(Continued)

(52) U.S. Cl.
CPC ....... *A61N 1/37223* (2013.01); *A61H 39/002* (2013.01); *A61N 1/0551* (2013.01); *A61N 1/37205* (2013.01); *A61N 1/37247* (2013.01); *A61N 1/37276* (2013.01); *H04W 48/10* (2013.01); *H04W 52/0235* (2013.01); *A61H 23/0218* (2013.01); *A61H 2039/005* (2013.01); *A61H 2201/0157* (2013.01); *A61H 2201/1207* (2013.01); *A61H 2201/165* (2013.01); *A61H 2201/5012* (2013.01); *A61H 2201/5033* (2013.01); *A61H 2201/5038* (2013.01);
(Continued)

(58) Field of Classification Search
CPC ............ A61N 1/37211; A61N 1/37217; A61N 1/37223; A61N 1/37252; A61N 1/3727
See application file for complete search history.

(56) References Cited

U.S. PATENT DOCUMENTS 5,722,998 A * 3/1998 Prutchi ............. A61N 1/37217
324/207.21
9,198,828 B2 * 12/2015 Greiner ............. A61N 1/36096
(Continued)

*Primary Examiner* — Eric D. Bertram
(74) *Attorney, Agent, or Firm* — ALG Intellectual Property, LLC

(57) ABSTRACT

An exemplary subcutaneous medical device implanted within a patient uses a coil-less magnetic field sensor included within the subcutaneous medical device to detect a toggling sequence between a presence and an absence of an externally-generated static magnetic field. The toggling sequence is representative of a digital data stream according to a digital wireless communication protocol. The subcutaneous medical device identifies, based on the detected toggling sequence and in accordance with the digital wireless communication protocol, a multi-bit command encoded within the digital data stream represented by the toggling sequence. The subcutaneous medical device further performs, in response to the identifying of the multi-bit command, an action associated with the multi-bit command. Corresponding methods and a corresponding external controller are also disclosed.

20 Claims, 16 Drawing Sheets

(51) Int. Cl.
*H04W 52/02* (2009.01)
*H04W 48/10* (2009.01)
*A61H 39/00* (2006.01)
*A61N 1/05* (2006.01)
*A61H 23/02* (2006.01)
*H05K 3/32* (2006.01)

(52) U.S. Cl.
CPC ............... *A61H 2201/5043* (2013.01); *A61H 2201/5058* (2013.01); *A61H 2201/5066* (2013.01); *A61H 2201/5097* (2013.01); *H05K 3/325* (2013.01); *H05K 2201/09027* (2013.01); *H05K 2201/10037* (2013.01); *Y02D 70/00* (2018.01)

(56) References Cited

U.S. PATENT DOCUMENTS

| | | | |
|---|---|---|---|
| 9,433,788 B2* | 9/2016 | Greiner | A61N 1/3606 |
| 2003/0171790 A1* | 9/2003 | Nelson | A61N 1/08 607/60 |
| 2004/0052392 A1* | 3/2004 | Sacha | H04R 25/43 381/331 |
| 2014/0214117 A1* | 7/2014 | Greiner | A61N 1/36096 607/45 |

* cited by examiner

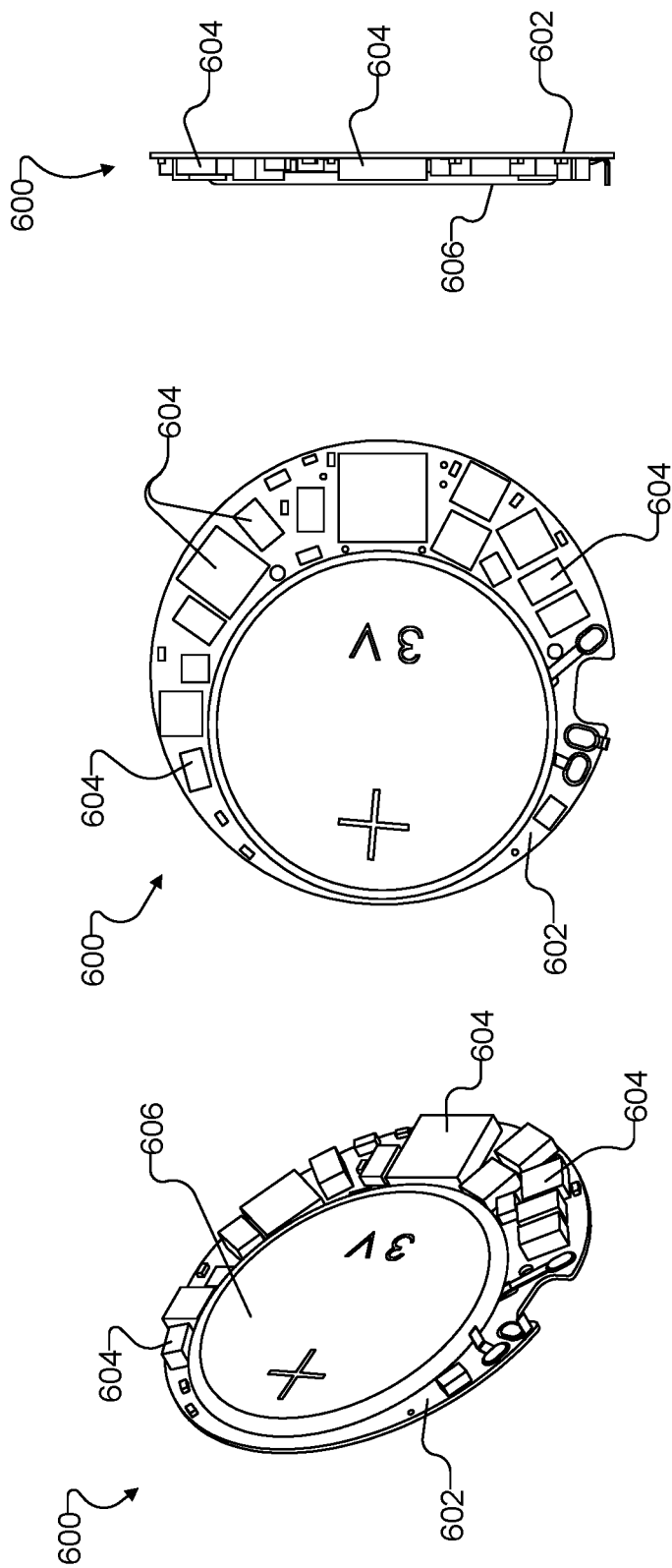

| FIFO Pattern | Minimum Form |
|---|---|
| 0000 0000 0011 | 0000 0001 0011 |
| 0000 0001 0110 | 0000 0001 0011 |
| 0000 0010 1100 | 0000 0001 0011 |
| 0000 0100 1000 | 0000 0001 0011 |
| 0000 1001 0000 | 0000 0001 0011 |
| 0001 0011 0000 | 0000 0001 0011 |
| 0010 0110 0000 | 0000 0001 0011 |
| 0100 1100 0000 | 0000 0001 0011 |
| 1001 1000 0000 | 0000 0001 0011 |
| 0011 0000 0001 | 0000 0001 0011 |
| 0110 0000 0010 | 0000 0001 0011 |
| 1100 0000 0100 | 0000 0001 0011 |
| 1000 0000 1001 | 0000 0001 0011 |

METHODS AND SYSTEMS FOR WIRELESS COMMUNICATION WITH A SUBCUTANEOUS MEDICAL DEVICE

RELATED APPLICATIONS

The present application claims priority under 35 U.S.C. § 119(e) to U.S. Provisional Patent Application No. 62/209,875, filed Aug. 25, 2015. The contents of the provisional patent application are hereby incorporated by reference in their entirety.

BACKGROUND INFORMATION

Subcutaneous medical devices may be implanted within patients (e.g., under the skin of patients) for various purposes including treatment of various conditions, disorders, diseases, and/or other maladies. For example, one type of subcutaneous medical device may be a subcutaneous neuromodulation system that includes (e.g., is implemented by) a coin-sized and coin-shaped electroacupuncture ("EA") device implanted beneath a skin surface of a patient at an acupoint. The EA device may include an electrode configuration (e.g., a central electrode of a first polarity centrally located on a surface of a housing of the EA device, and an annular electrode of a second polarity and that is spaced apart from the central electrode) that is configured to deliver stimulation pulses to tissue of the patient at the acupoint in accordance with a stimulation regimen in order to treat a condition, disorder, disease, and/or other malady associated with the acupoint.

In some examples, it may be desirable to communicate with a subcutaneous medical device implanted within a patient from a location external to the patient. For example, it may be desirable for a person (e.g., a physician or other medical practitioner associated with the patient, the patient, etc.) to be able to easily, accurately, conveniently, and/or non-invasively control the subcutaneous medical device to, for instance, turn the device ON or OFF, start or stop particular operations of the device (e.g., start or stop stimulation sessions), modify characteristics of device operation (e.g., intensity, duration, and/or other characteristics of stimulation sessions being applied), and so forth.

Unfortunately, conventional forms of wireless communication, where information is modulated onto electromagnetic carrier waves and transmitted and received using antennas, may present challenges in the context of wireless communication with subcutaneous medical devices. For example, subcutaneous medical devices may be extremely small (e.g., coin-sized) such that components (e.g., antenna coils, etc.) required for conventional wireless interfaces may not fit within a housing of the subcutaneous medical devices. Additionally, subcutaneous medical devices may use power extremely judiciously (e.g., so that a single-use battery may power the subcutaneous medical device for several years without being replaced), and it may be difficult or impossible to implement a conventional wireless communication interface under such stringent power usage restrictions.

Certain subcutaneous medical devices have avoided the problems associated with conventional wireless communication interfaces by providing some amount of control based on externally-generated static magnetic fields, which may be detected by the subcutaneous medical devices using very small and low-power components. However, operations controllable using only a presence or an absence of a static magnetic field have been limited to binary, ON/OFF-type operations. It would be desirable to be able to send more complex and varied commands to the subcutaneous medical device.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 6A, 6B, and 6C illustrate exemplary views of an electronic assembly adapted to fit inside of a housing of the EA device illustrated in FIG. 2 according to principles described herein.

FIG. 12 illustrates an exemplary conversion table wherein bit sequences are converted to a minimum form according to principles described herein.

DETAILED DESCRIPTION

Figure 1:
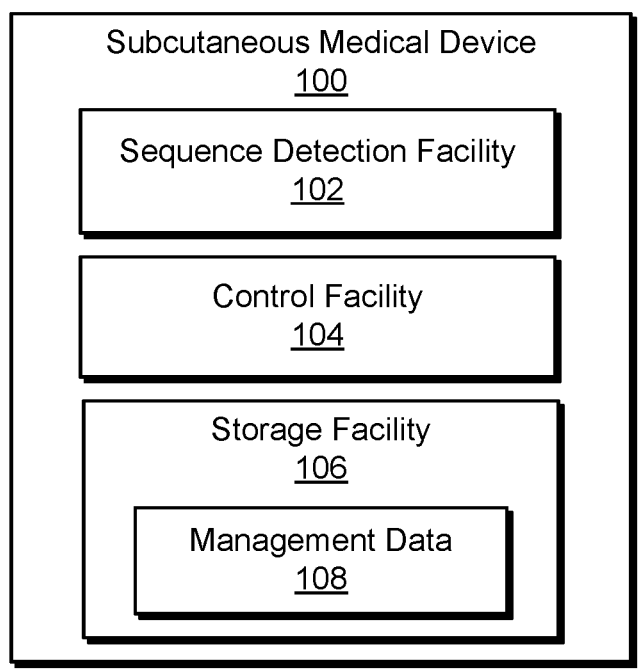
FIG. 1 illustrates exemplary components of an exemplary subcutaneous medical device configured to receive wireless communication according to principles described herein.

Methods and systems of wireless communication with a subcutaneous medical device are described herein. For example, as will be described in more detail below, a subcutaneous medical device implanted within a patient may detect a toggling sequence between a presence and an absence of an externally-generated static magnetic field. The subcutaneous medical device may use a coil-less magnetic field sensor (e.g., an anisotropic magnetoresistance ("AMR") sensor, a Hall effect sensor, a Reed switch, etc.) included within the subcutaneous medical device to detect the toggling sequence. The toggling sequence may be representative of a digital data stream according to a digital wireless communication protocol.

Based on the detecting of the toggling sequence and in accordance with the digital wireless communication protocol, the subcutaneous medical device may identify a multi-bit command encoded within the digital data stream represented by the toggling sequence. Then, in response to the identifying of the multi-bit command, the subcutaneous medical device may perform an action associated with the multi-bit command. Examples of digital wireless communication protocols, digital data streams associated with the digital wireless communication protocols, and multi-bit commands that may be encoded within the digital data streams will be provided below.

Wireless communication with a subcutaneous medical device that includes detecting toggling sequences of externally-generated static magnetic fields, identifying multi-bit commands encoded within digital data streams represented by the toggling sequences, and performing actions associated with the multi-bit commands, as described herein, may provide various advantages over conventional wireless communication interfaces. For example, because static magnetic fields can be detected by coil-less magnetic field sensors that are very small and/or consume very little power (e.g., in relation to antennas and other electrical components used to implement traditional wireless communication interfaces), subcutaneous medical devices implementing coil-less magnetic field sensors may be configured to be very small and to consume very little power, while still allowing for relatively sophisticated external control using multi-bit commands. More specifically, subcutaneous medical devices implementing coil-less magnetic field sensors may detect digital data streams with multi-bit commands while being completely contained within a coin-sized and coin-shaped housing, and/or while using so little power that a single-use battery built into the subcutaneous medical device may power the subcutaneous medical device for years without replacement.

Wireless communication with a subcutaneous medical device according to methods and systems described herein may also provide significant advantages over previous communications methods based on detection of externally-generated static magnetic fields using coil-less magnetic field sensors. In particular, rather than being limited to binary and/or simplistic ON/OFF-type direction from an external magnet, subcutaneous medical devices implementing the wireless communication described herein may receive multi-bit commands (e.g., selected from a command set that may include any of a large number of possible multi-bit commands) that allow for more sophisticated, convenient, and nuanced external control of the subcutaneous medical devices. Moreover, subcutaneous medical devices that accept binary, ON/OFF-type direction from magnets may inadvertently be affected (i.e., controlled) by static magnetic fields around the patient (e.g., caused by refrigerator magnets or the like) that may cause the subcutaneous medical devices to perform actions that may be undesirable (e.g., turning the device OFF, starting operation of the device at an undesirable time, etc.). The wireless communication described herein provides another significant advantage that a specific multi-bit access code (e.g., a twelve-bit code) may be required by a subcutaneous medical device prior to the subcutaneous medical device detecting and/or performing any other command, thus virtually eliminating any probability of inadvertent control from static magnetic fields in the vicinity of the user.

Various embodiments will now be described in more detail with reference to the figures. The disclosed methods and systems may provide one or more of the benefits mentioned above and/or various additional and/or alternative benefits that will be made apparent herein.

FIG. 1 illustrates exemplary components of an exemplary subcutaneous medical device ("device 100") configured to receive wireless communication. As will be described in more detail below, in certain implementations, device 100 may only receive wireless communication (e.g., a downlink from an external controller), while in other implementations device 100 may also send wireless communications (e.g., an uplink back to the external controller).

As shown in FIG. 1, device 100 may include, without limitation, a sequence detection facility 102, a control facility 104, and a storage facility 106 selectively and communicatively coupled to one another. It will be recognized that although facilities 102 through 106 are shown to be separate facilities in FIG. 1, facilities 102 through 106 may be combined into fewer facilities, such as into a single facility, or divided into more facilities as may serve a particular implementation. Each of facilities 102 through 106 will now be described in more detail.

Sequence detection facility 102 may detect, capture, buffer, or otherwise handle or process toggling sequences between a presence and an absence of an externally-generated static magnetic field. For example, an external magnet may provide a static magnetic field that appears and disappears at the location where device 100 is implanted within the patient to generate a type of static magnetic "signal" in which information may be encoded. In some examples, an external magnet such as an electromagnet near device 100 may be energized (e.g., turned ON) and de-energized (e.g., turned OFF) to generate the presence and the absence of the static magnetic field, respectively. Similarly, a permanent magnet may be physically brought near device 100 and then moved away again to provide the presence and the absence of the static magnetic field.

Regardless of how the externally-generated static magnetic field is provided, sequence detection facility 102 may detect a toggling sequence between a presence and an absence of the externally-generated static magnetic field and interpret the toggling sequence as a digital data stream according to a digital wireless communication protocol. For example, as will be described in more detail below, sequence detection facility 102 may interpret the digital data stream to include a sequence of bits such as zero bits, one bits, and/or other bits (e.g., FIFO_CLEAR bits), based on a digital wireless communication protocol known to sequence detection facility 102 and to an external controller generating toggling sequence. Sequence detection facility 102 may also buffer and/or otherwise facilitate processing of the bits interpreted from the toggling sequence. For example, sequence detection facility 102 may include one or more first-in-first-out ("FIFO") buffers (e.g., four-bit buffers, twelve-bit buffers, etc.) that may shift each bit into a computer-usable form within the FIFO buffer as the bit is interpreted based on the toggling sequence.

Control facility 104 may receive the digital data stream (e.g., the sequence of bits interpreted by sequence detection facility 102) by, for example, reading the bits buffered within the one or more FIFO buffers. Based on the received digital data stream, control facility 104 may identify a multi-bit command encoded within the digital data stream. For example, as will be described in more detail below, control facility 104 may convert a number of bits (e.g., twelve bits stored in a twelve-bit FIFO buffer) into a minimum form and compare the minimum form of the bits with minimum forms of known commands. In other examples, control facility 104 may obtain the command by waiting for a FIFO_CLEAR bit and then reading in the bits arriving thereafter. Once a multi-bit command encoded within the digital data stream has been identified, control facility 104 may perform an action associated with the multi-bit command. Exemplary actions associated with exemplary multi-bit commands will be described in more detail below.

Storage facility 106 may maintain system management data 108 and/or any other data received, generated, managed, maintained, used, and/or transmitted by facilities 102 or 104 in a particular implementation. Management data 108 may include digital data stream data, multi-bit command data, device state data, and so forth, as may be used by facilities 102 or 104 in a particular implementation. In some examples, storage facility 106 may include or be implemented by solid state memory, solid-state buffers, and/or other types of data storage as may serve a particular implementation.

Device 100 may include or be implemented by any type of subcutaneous medical device as may serve a particular implementation. For example, device 100 may include or be implemented by a subcutaneous neuromodulation system including a coin-sized and coin-shaped electroacupuncture device implanted beneath a skin surface of the patient at an acupoint. In this example, the electroacupuncture device may have an electrode configuration thereon that is configured to deliver stimulation pulses to tissue of the patient at the acupoint in accordance with a stimulation regimen. For instance, the electrode configuration may include a central electrode of a first polarity centrally located on a surface of a housing of the electroacupuncture device, and may further include an annular electrode of a second polarity and that is spaced apart from the central electrode.

The stimulation regimen of the electroacupuncture device may include a plurality of stimulation sessions in which the tissue of the patient at the acupoint is stimulated. For example, the stimulation sessions may each having a duration of T3 minutes and may occur at a rate of once every T4 minutes, such that a duty cycle of the stimulation sessions is a ratio of T3 to T4 and is less than 0.05.

Figure 2:
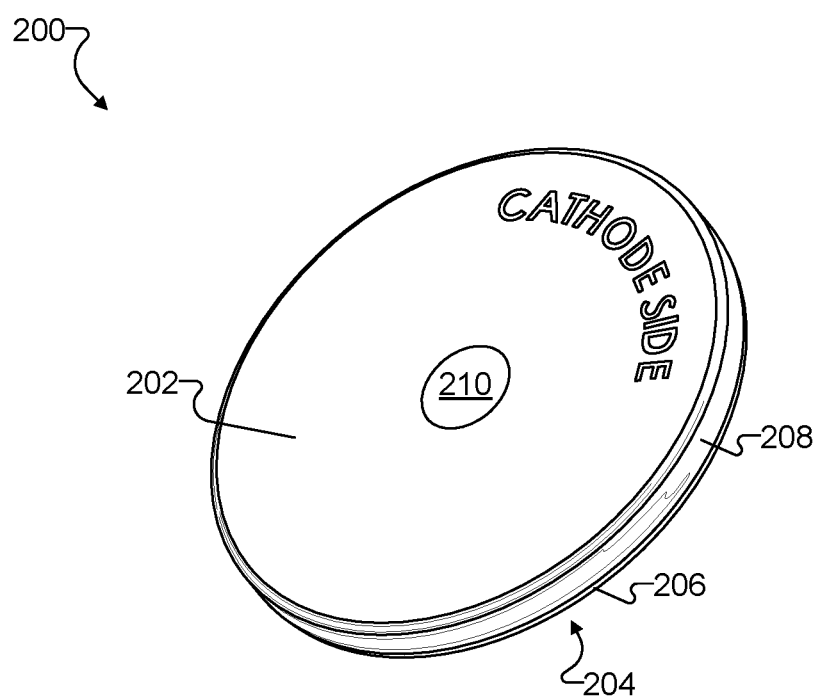
FIG. 2 illustrates a perspective view of an exemplary leadless implantable electroacupuncture ("EA") device configured to be implanted subcutaneously within a patient and configured to receive wireless communication according to principles described herein.

To illustrate, FIG. 2 shows a perspective view of an exemplary leadless implantable electroacupuncture device ("EA device 200") configured to be implanted subcutaneously within a patient and configured to receive wireless communication according to the methods described herein.

As shown, EA device 200 may have the appearance (i.e., the approximate size and shape) of a disc or coin (e.g., having a diameter of approximately 23 mm, and a thickness of approximately 2 to 3 mm), and may include a bottom side 202, a top side 204, and an edge 206. In order to function properly, EA device 200 may include various components located (e.g., hermetically sealed) within a housing of EA device 200 provided by bottom side 202, top side 204, and edge 206. For example, EA device 200 may include pulse generation circuitry configured to deliver stimulation sessions to the patient's body tissue at a specified acupoint (e.g., to a particular nerve associated with the specified acupoint), a primary battery configured to provide operating power for EA device 200 to function, a communication subsystem (e.g., a coil-less magnetic field sensor and/or a pickup coil) for receiving and responding to operating commands (e.g., multi-bit commands) wirelessly communicated to EA device 200 from an external (i.e., non-implanted) location, and/or any other components that may serve a particular implementation.

To generate a stimulation session, EA device 200 may include an annular electrode 208 placed around a perimeter of edge 206, and a central electrode 210 centrally located on bottom side 202, as shown in FIG. 1. Annular electrode 208 may serve as an anode electrode and central electrode 210 may serve as a cathode electrode, or vice versa. Additionally, an insulating later (not explicitly shown) may be included around edge 206 between edge 206 and annular electrode 208, and a layer of silicone molding (not explicitly shown) may cover some or all of the housing of EA device 200 (e.g., bottom side 202, top side 204, and edge 206). For example, silicone molding may be used to insulate the entire housing of EA device 200, leaving only annular electrode 208 and central electrode 210 exposed in order to better control electric fields established between annular electrode 208 and central electrode 210 and to prevent the entire housing of EA device 200 from acting as a cathode electrode.

In operation, EA device 200 may be implanted below the skin surface of the patient at a specified acupoint and may generate stimulation sessions in accordance with a specified stimulation regimen. For example, the stimulation regimen may prescribe that a relatively short series of stimulation pulses be applied to the specified acupoint during a short session (e.g., a thirty-minute session) that is separated by a relatively long period of time (e.g., seven days) from other stimulation sessions. As such, a duty cycle of the stimulation sessions may be very low (e.g., less than 0.05). Additionally, a duty cycle of the stimulation pulses applied during a stimulation may also be very low.

As shown, one advantage of EA device 200 may be a simple, leadless design. Specifically, electrodes 208 and 210 may be directly attached to the housing of EA device 200 rather than to leads configured to be positioned and anchored at desired stimulation sites away from the location that EA device 200 is implanted. As a result, implanting EA device 200 within a patient may be less invasive and/or less risky to the patient than implant procedures for implants having leads that must be tunneled through body tissue or blood vessels to reach desired stimulation sites. In other implementations, other types of implantable stimulators (e.g., implantable stimulators with leads connected thereto) may also be used in accordance with the methods and systems described herein. For example, stimulation sessions to a particular nerve may be performed by applying the stimulation sessions by way of an electrode included on a lead connected to EA device 200.

Figure 3:
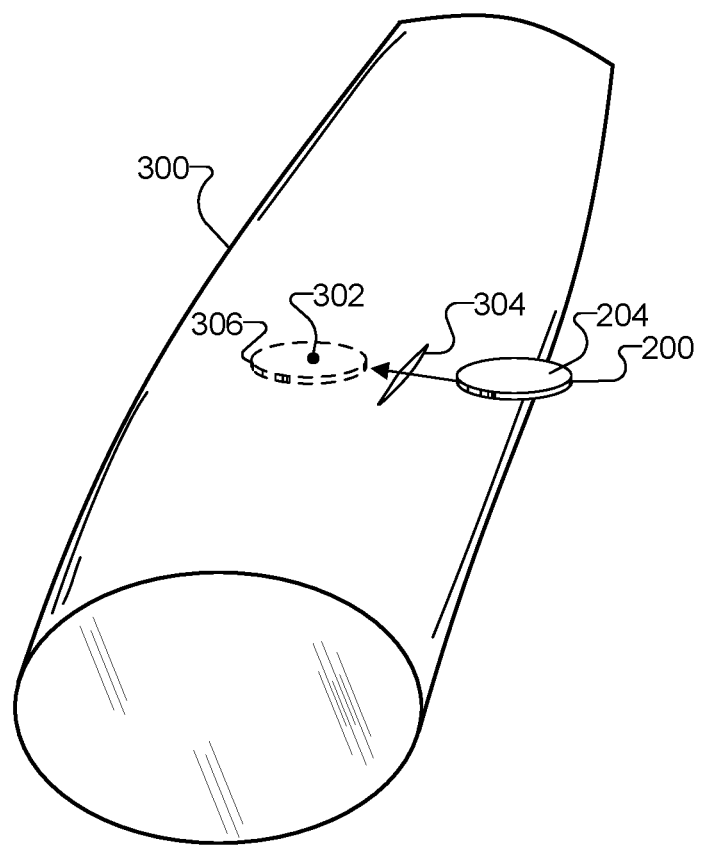
FIG. 3 illustrates a view of a limb of a patient where a specified acupoint has been identified and selected, and illustrates a manner of implanting a subcutaneous medical device at the selected acupoint according to principles described herein.

FIG. 3 shows a view of a limb 300 of a patient (e.g., an arm or leg of the patient) where a specified acupoint has been identified and selected, and illustrates a manner of implanting a subcutaneous medical device at the selected acupoint. More specifically, a specified acupoint 302 (e.g., an acupoint known to moderate or affect a particular condition of the patient) may have been identified and selected in limb 300 to receive electroacupuncture treatment. Accordingly, FIG. 3 illustrates a manner of implanting EA device 200 at acupoint 302 to provide the electroacupuncture treatment to acupoint 302. In particular, an incision 304 may be made into limb 300 near (e.g., 10 to 15 mm away from) acupoint 302. A slot may be formed at incision 304 (e.g., by lifting up the skin closest to acupoint 302) and a pocket 306 may thus be formed under the skin at the location of acupoint 302 to receive EA device 200. Subsequently, with top side 204 facing up (i.e., facing the skin), EA device 200 may be slid through the slot of incision 304 and into pocket 306 so that EA device 200 is centered at specified acupoint 302. Then, with EA device 200 in place, incision 304 may be sewn up or otherwise closed and EA device 200 may be left under the patient's skin at the location of acupoint 302 so that subcutaneous neuromodulation therapy may be performed by applying stimulation sessions as described herein. Advantageously, the implantation surgery of EA device 200 may often be completed in less than ten minutes in an outpatient setting or in a doctor's office. Only minor, local anesthesia may be used and no significant risks may be associated with the implant procedure. Also, if desired, EA device 200 may be quickly explanted in a similarly safe and easy surgical procedure.

Figure 4:
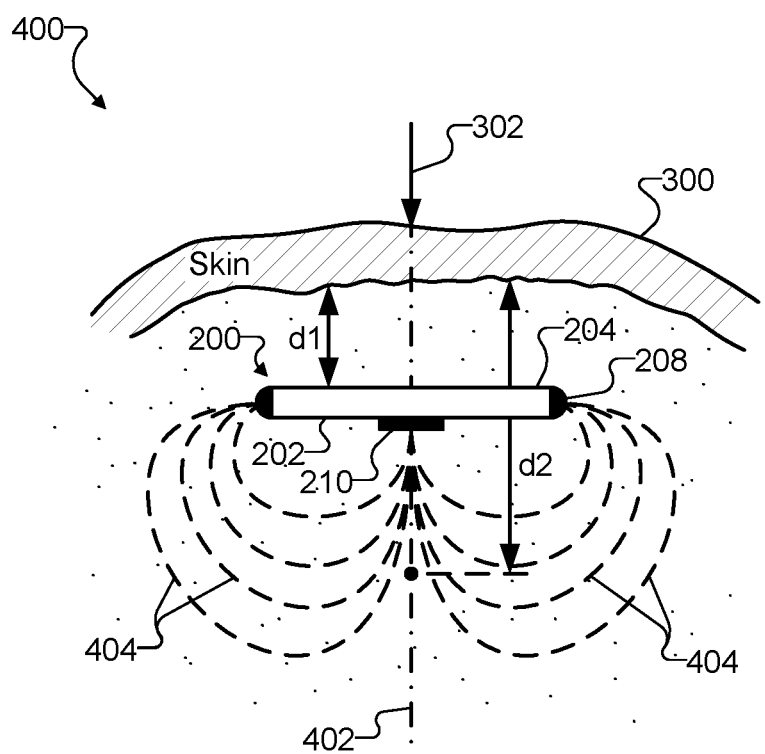
FIG. 4 illustrates a cross-sectional view of a subcutaneous medical device implanted at a selected acupoint within a patient according to principles described herein.

FIG. 4 illustrates a cross-sectional view 400 of a subcutaneous medical device implanted at a selected acupoint within a patient. More particularly, view 400 shows EA device 200 implanted at acupoint 302 within limb 300 of the patient. As shown, EA device 200 may be implanted at a depth d1 under the skin (e.g., approximately 2 mm to 4 mm under the skin). Top side 204 of EA device 200 may be facing up to the skin of the patient, while bottom side 202 of EA device 200, upon which central electrode 210 is disposed, may be facing down away from the skin. As illustrated by cross-sectional view 400, EA device 200 may provide a symmetrical electrode configuration where central electrode 210 is centrally located on an acupoint axis 402 extending orthogonally into the skin from a location on the skin where acupoint 302 is indicated, and where annular electrode 208, which may be implemented as a ring electrode, encircles central electrode 210 and acupoint axis 402.

The symmetry between central electrode 210 at the center and annular electrode 208 encircling central electrode 210 may help focus an electric field generated by electrodes 208 and 210, promoting stimulation current generated by application of a stimulation pulse to flow into tissue below the central electrode, where it may be desired that electroacupuncture stimulation should be applied. For example, while acupoint 302 is illustrated in FIGS. 3 and 4 as being on the surface of the skin, electroacupuncture treatment may be most effective at a distance d2 below the skin surface along acupoint axis 402. The ideal distance d2 may vary depending upon where the acupoint is located on the body and/or depending on an aim of the acupuncture treatment to be performed.

Also illustrated in view 400 are electric field gradient lines 404, which may be created by an electroacupuncture pulse applied to tissue within the patient by annular electrode 208 and/or central electrode 210. As shown, electric field gradient lines 404 are strongest along a line coinciding with, or near to, acupoint axis 402. Accordingly, FIG. 4 illustrates that one of the primary advantages of the symmetrical electrode configuration of EA device 200 is that the precise orientation of EA device 200 within the patient is not important. Rather, as long as EA device 200 is centered at acupoint 302 (i.e., such that acupoint axis 402 passes through the center of EA device 200) and central electrode 210 is facing down, a strong electric field (e.g., illustrated by electric field gradient lines 404) may be generated to align with acupoint axis 402. As a result, EA stimulation current may flow along (or very near) acupoint axis 402, and the desired electroacupuncture stimulation may properly be applied to the tissue at a depth d2 below the acupoint 302 location indicated on the skin.

Figure 5A:
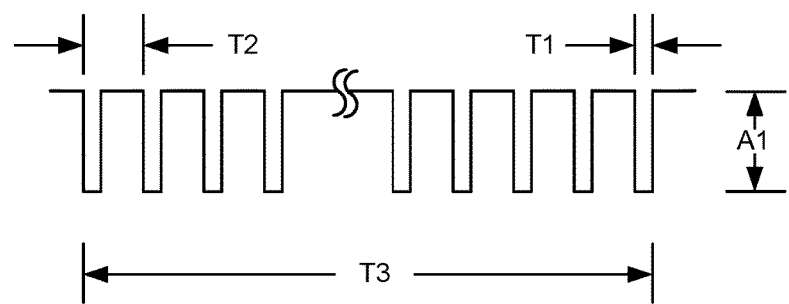
FIGS. 5A and 5B illustrate exemplary timing waveform diagrams showing exemplary stimulation parameters used by the EA device illustrated in FIG. 2 to generate stimulation pulses according to principles described herein.
Figure 5B:
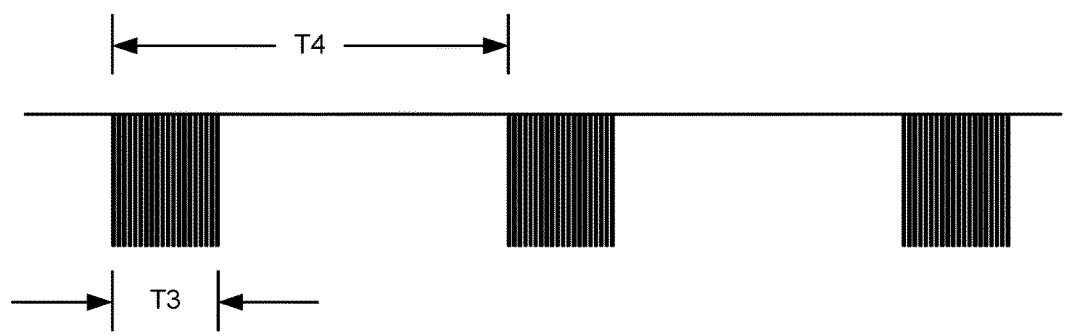

FIGS. 5A and 5B show timing waveform diagrams illustrating exemplary EA stimulation parameters used by EA device 200 to generate stimulation pulses. As seen in FIG. 5A, four stimulation parameters may be associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01, but may, in some instances, be as much as 0.03. The duration of a stimulation session is dictated or defined by the time period T3, and may be, for example, at least 10 minutes and less than 60 minutes. The amplitude of the stimulation pulses is defined by the amplitude A1. This amplitude may be expressed in either voltage or current.

FIG. 5B illustrates the manner in which the stimulation sessions are administered in accordance with a specified stimulation regimen. FIG. 5B shows several stimulation sessions of duration T3, and how often the stimulation sessions occur. The stimulation regimen thus includes a time period T4 which sets the time period from the start of one stimulation session to the start of the next stimulation session and may be, for example, at least 1440 minutes. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4(min). Then, as time goes on, the value of T4 may be gradually increased until a desired value of T4, T4(final), is reached.

By way of example, if T4(min) is 1 day, and T4(final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described above, an enhancement is to use a table that defines session durations and intervals whereby the automatic session interval can be shorter for the first week or so. For example, if T3 is 30 minutes, the first 30-minute session may be delivered after 1 day, the second 30-minute session may be delivered after 2 days, the third 30-minute session may be delivered after 4 days, and the fourth 30-minute session may be delivered for all subsequent sessions after 7 days. If a triggered session is delivered completely, it advances the therapy schedule to the next table entry.

By way of example, one exemplary set of parameters that could be used to define a stimulation regimen is as follows:
T1=0.5 milliseconds
T2=500 milliseconds
T3=30 minutes
T4=7 days (10,080 minutes)
A1=15 volts (across 1 KΩ), or 15 milliamps (mA)

An example of typical ranges for each parameter for treating an exemplary condition may be as follows:
T1=0.1 to 2.0 milliseconds (ms)
T2=67 to 1000 ms (15 Hz to 1 Hz)
T3=20 to 60 minutes
T4=1,440 to 10,080 minutes (1 day to 1 week)
A1=1 to 15 mA The values shown above for the stimulation regimen and ranges of stimulation parameters for use within the stimulation regimen are only exemplary. In some examples, the parameters above may be specifically configured to treat a particular condition, disease, disorder, or other malady. For example, EA device 200 may receive one or more multi-bit commands from an external controller according to wireless communication methods and techniques described herein to set any of the parameters described above to appropriate values configured to treat the particular malady. As such, EA device 200 may perform the stimulation sessions in accordance with the received commands. The external device may communicate the control command in any way as may serve a particular implementation. For example, receiving the control command may include detecting, using a coil-less magnetic field sensor included in EA device 200, an externally-generated static magnetic field generated by the external controller, as will be described in more detail below.

In some examples, the ratio of T3 to T4 may be specified (e.g., by the control command) to be very low (e.g., no more than 0.05). Maintaining a low duty cycle of this magnitude may represent a significant change as compared to other subcutaneous medical devices. For example, by using a very low duty cycle, a small battery (e.g., a coin-sized cell) with a relatively high internal impedance (e.g., at least 5 ohms) may be used to provide power to EA device 200 for a long period of time (e.g., several years). One benefit of such a small battery, in turn, is that the housing of EA device 200 may be compact and small, allowing EA device 200 to be implanted and used with or without leads. As such, EA device 200 may be relatively easy to implant at the desired stimulation site (e.g., acupoint) as long as the frequency and duration of stimulation sessions are limited.

Limiting the frequency and duration of the stimulation sessions may be beneficial because doing so may account for the fact that some treatments are best done slowly and methodically, over time, rather than quickly and harshly using large doses of stimulation (or other treatments) aimed at forcing a rapid change in the condition of the patient. In addition, a slow and methodical conditioning is consistent with the time scale for remodeling of the central nervous system needed to produce a sustained therapeutic effect.

FIGS. 6A, 6B, and 6C illustrate exemplary views of an electronic assembly adapted to fit inside of a housing of EA device 200. Specifically, FIG. 6A illustrates a perspective view of an electronic assembly 600 that may be enclosed by (e.g., hermetically sealed within) a housing of EA device 200. As shown, electronic assembly 600 may include a multi-layer printed circuit (PC) board 602, or equivalent mounting structure, as well as various electronic components 604 and a battery 606 that may be mounted on PC board 602. FIGS. 6B and 6C show a plan view and side view, respectively, of electronic assembly 600. As illustrated, electronic components 604 may be assembled and connected together so as to perform proper circuit functions to allow EA device 200 to perform its intended functions. The circuit functions performed by electronic components 604 (i.e., by electronic assembly 600) will be explained in more detail below.

Figure 7:
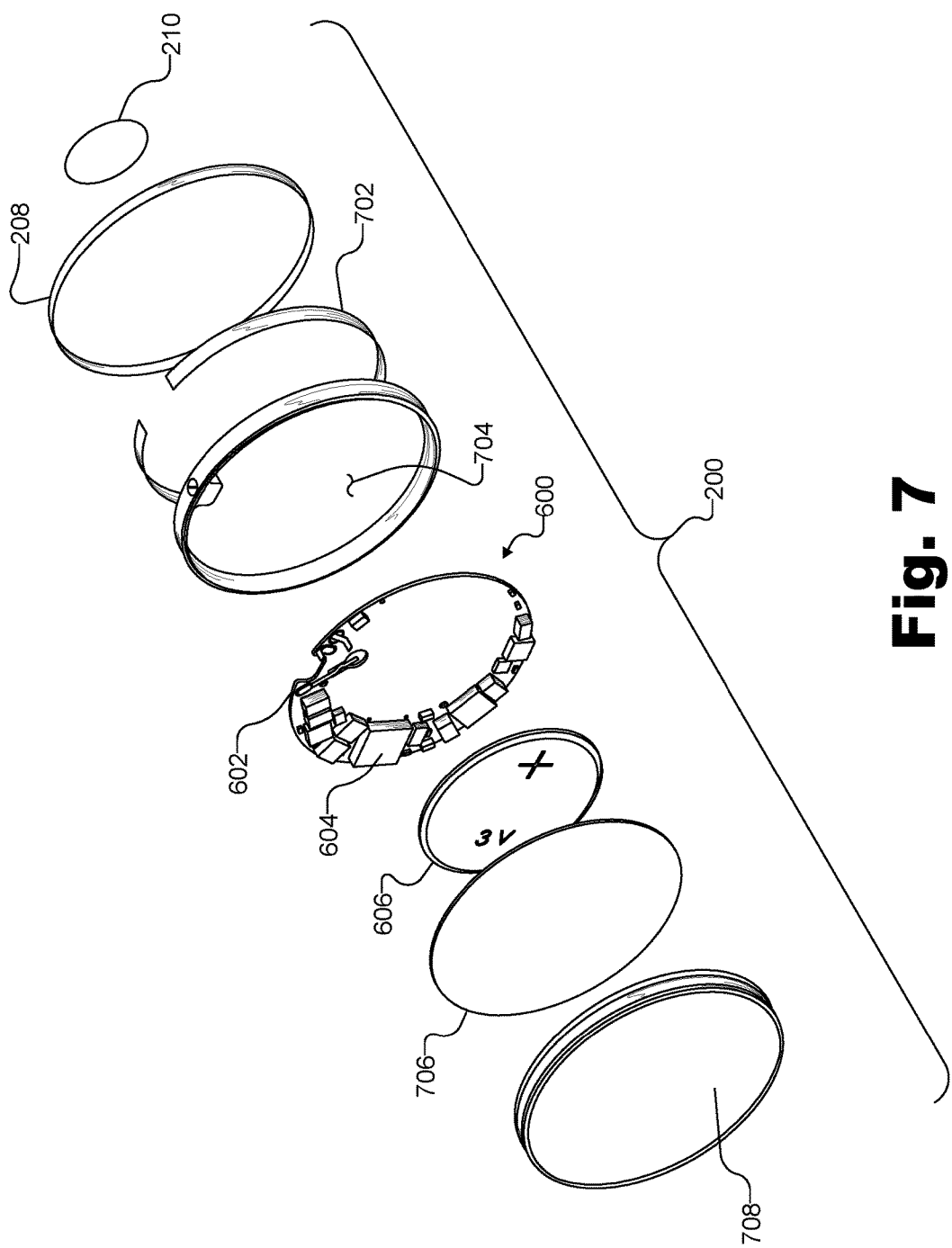
FIG. 7 illustrates an exemplary exploded view of the EA device illustrated in FIG. 2, showing various constituent parts of the EA device according to principles described herein.

FIG. 7 illustrates an exemplary exploded view of EA device 200 showing various constituent parts of EA device 200. As illustrated in FIG. 7, EA device 200 may include, starting from the right and moving toward the left, central electrode 210 (e.g., a cathode electrode), annular electrode 208 (e.g., an anode electrode), an insulating layer 702, a bottom case 704 (i.e., a "can" portion of the housing of EA device 200), electronic assembly 600 (e.g., including battery 606 and electronic components 604 mounted on PC board 602), cover plate 706, and a layer of silicon molding 708.

While certain details may not be fully illustrated in FIG. 7, it will be understood that the components illustrated in FIG. 7 may be assembled in any way as may serve a particular implementation, including in any way described herein. For example, cover plate 706 may be connected to bottom case 704 in any suitable way. For example, cover plate 706 may be welded to the edge of bottom case 704 (e.g., using laser beam welding or another equivalent process), as one of the final steps in the assembly process.

Additionally, other components not necessarily shown or identified in FIG. 7 may be included in the assembly of EA device 200. For example, EA device 200 may include adhesive patches for bonding battery 606 to PC board 602 of electronic assembly 600, and/or for bonding electronic assembly 600 to the inside of bottom case 704. To prevent high temperature exposure of battery 606 during the assembly process, conductive epoxy may be used to connect a battery terminal to PC board 602.

The layer of silicone molding 708 may be used to cover all the surfaces of EA device 200 except for annular electrode 208 and central electrode 210. In certain examples, an over-molding process may be used to apply the layer of silicone molding 708. For example, over-molding processes may be used such as: (a) molding a silicone jacket and gluing the jacket onto bottom case 704 using room temperature cure silicone (RTV) inside of a mold, and curing at room temperature; (b) injecting room temperature cure silicone in a mold formed from a material with excellent mechanical and/or chemical properties that are retained at high temperatures such that the silicone will not stick to the material (e.g., a PEEK or Teflon® mold); or (c) dip coating EA device 200 in room temperature cure silicone while masking the electrode surfaces that are not to be coated.

When assembled, insulating layer 702 may be positioned underneath annular electrode 208 so that anode electrode 208 does not short to bottom case 704. Similarly, the electrical contact with central electrode 210 may be made through bottom case 704. However, because EA device 200 may be coated with the layer of silicone molding 708 everywhere besides annular electrode 208 and central electrode 210, all stimulation current generated by EA device 200 may be forced to flow between the exposed surfaces of the anode and cathode (i.e., between annular electrode 208 and central electrode 210).

As mentioned above, it will be understood that, while the configuration described herein uses annular electrode 208 as an anode electrode and central electrode 210 as a cathode electrode, this arrangement may be reversed in certain examples. For example, in certain implementations, the ring electrode (i.e., annular electrode 208) may serve as a cathode electrode while a circular, central electrode (i.e., central electrode 210) may serve as an anode electrode. Moreover, the location and shape of electrodes 108 and 110 may be configured differently than is shown in the implementations described above. For example, in certain implementations, annular electrode 208 may not be placed around the perimeter of the device, but rather may be a flat circumferential electrode that assumes different shapes (e.g., round or oval) and is placed on the front or back surface (i.e., bottom side 202 or top side 204) of EA device 200 so as to surround central electrode 210. Additionally, the same or other implementations, the surfaces of the anode and/or cathode electrodes (e.g., annular electrode 208 and/or central electrode 210) may have convex surfaces.

Moreover, while the implementation illustrated herein incorporates a round, short cylindrical-shaped housing (i.e., referred to as a "coin-shaped" housing), it will be understood that other implementations may employ different shapes for the container (e.g., bottom case 704), and/or the associated cover plate (e.g., cover plate 706). For example, bottom case 704 may be oval-shaped, rectangular-shaped (e.g., square with smooth corners), polygonal-shaped (e.g., hexagon-, octagon-, or pentagon-shaped), button-shaped (with convex top or bottom for a smoother profile), or shaped in any other way as may serve a particular implementation. Any of these alternate shapes, or others, would still permit EA device 200 to provide a robust, compact, thin, case to house the electronic circuitry and the power source used by EA device 200, and would still allow the thin device to provide the benefits described herein related to its manufacture, implantation, and use. In particular, as long as EA device 200 remains relatively thin (e.g., less than approximately 2-3 mm) and does not have a maximum linear dimension greater than approximately 25 mm, EA device 200 may be readily implantable in a pocket over the tissue area where a selected acupuoint is located.

While EA device 200 has been described in detail as one example of a subcutaneous medical device with which wireless communication described herein (i.e., multi-bit wireless communication using toggling sequences between the presence and absence of externally-generated static magnetic fields) may be performed, it will be understood that device 100 may include or be implemented by various other types of subcutaneous medical devices in various implementations (e.g., types other than subcutaneous neuromodulation devices or EA devices such as EA device 200). Specific examples of multi-bit wireless communication with device 100 will now be described. For convenience, the form and basic operation of device 100 will be illustrated and described in the following examples as if device 100 includes, is implemented by, or is at least similar to EA device 200. However, it will be understood that the wireless communication principles being illustrated and described may also apply to various other types of subcutaneous medical devices that may implement or be included within device 100 in various implementations.

As mentioned above, in certain examples, an external controller may be located near a patient at a site where a subcutaneous medical device (e.g., device 100) is implanted within the patient. The external controller may detect a manipulation by a user (e.g., a medical practitioner associated with the patient) of one or more user controls associated with a user interface of the external controller. Based on the detecting of the manipulation of the one or more user controls, the external controller may determine one or more commands indicated by the user for the external controller to encode within a digital data stream to be transmitted to the subcutaneous medical device according to a digital wireless communication protocol. Accordingly, based on the determining of the one or more commands, the external controller may generate a toggling sequence between a presence and an absence of a static magnetic field (e.g., a toggling sequence detectable by device 100 using a coil-less magnetic field sensor included within device 100). For example, the toggling sequence may be representative of the digital data stream and may encode a multi-bit command representative of one of the one or more commands and that, when identified by device 100, causes device 100 to perform an action associated with the multi-bit command. In certain examples, the toggling sequence may be generated using an electromagnet within the external controller that creates the presence of the static magnetic field when the electromagnet is energized and creates the absence of the static magnetic field when the electromagnet is de-energized.

Figure 8:
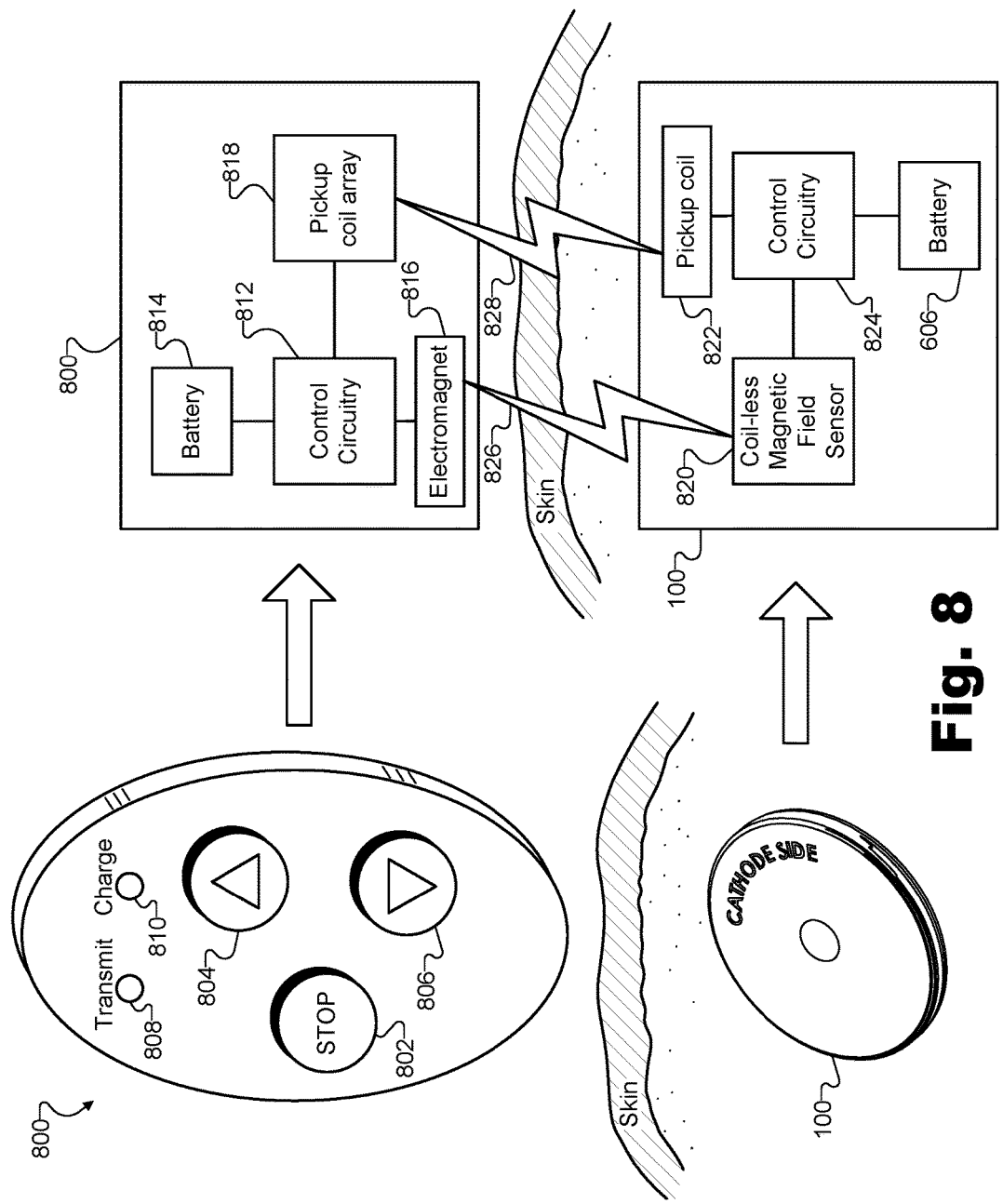
FIG. 8 illustrates exemplary wireless communication between an exemplary external controller located near a patient at a site where an exemplary subcutaneous medical device is implanted within the patient according to principles described herein.

To illustrate, FIG. 8 shows exemplary wireless communication between an exemplary external controller located near a patient at a site where an exemplary subcutaneous medical device is implanted within the patient. More specifically, FIG. 8 illustrates wireless communication between an external controller 800 that is located externally to (i.e., outside the skin of) the patient, and device 100, which is implanted within (i.e., under the skin of) the patient. On the left side of FIG. 8, functional illustrations of external controller 800 and device 100 are shown in order to illustrate external features such as user interface controls of external controller 800 and/or a coin-sized, coin-shaped housing of device 100. As shown, external controller 800 is on one side of the skin of the patient (i.e., outside the patient) while device 100 is on the other side (i.e., implanted within the patient). On the right side of FIG. 8, respective operational block diagrams of external controller 800 and device 100 are shown to illustrate interoperation of exemplary internal components of external controller 800 and device 100 as wireless communication between external controller 800 and device 100 is performed.

Referring first to the illustration of external controller 800 at the left, external controller 800 may include a simple user interface, such as an interface that includes just three buttons and/or two status LEDs. Specifically, as shown, external controller 800 may include a STOP button 802, an INCREASE button 804, and a DECREASE button 806, as well as a TRANSMIT indicator LED 808 and a CHARGE indicator LED 810. Accordingly, a user of external controller 800 such as a medical practitioner associated with the patient who is overseeing therapy sessions (e.g., electroacupuncture stimulation sessions) using device 100, may control device 100 using the user interface of external controller 800. In some examples, the buttons and LEDs of the user interface of external controller 800 may have overloaded functionality, such that one button or LED may be associated with (e.g., may trigger or indicate) a plurality of different functions or operations depending on the context.

For example, INCREASE button 804 may be used both to increase a parameter (e.g., stimulation level, duration, etc.) of therapy sessions delivered by device 100, as well as to "wake up" device 100 by entry of an access code (e.g., a twelve-bit access code). For example, if device 100 is new and was recently implanted within the patient, device 100 may be in a "shelf mode" in which device 100 is essentially turned off and will not perform any operations (e.g., therapy sessions) until otherwise instructed. As another example, if device 100 was previously implanted in the patient and is configured to perform stimulation sessions according to a stimulation regimen (e.g., weekly 30-minute stimulation sessions), device 100 may be in a "sleep mode" in which device 100 is essentially turned off and will not perform any operations (e.g., therapy sessions) until the next scheduled session arrives according to the stimulation regimen (e.g., which may be in several days). In either case, in order to conserve battery power, device 100 may normally be configured to sleep and ignore toggling sequences or other static magnetic fields in the vicinity of device 100). However, periodically (e.g., once every 10 seconds), device 100 may be configured to briefly enter a waking mode where device 100 attempts to detect a presence of a static magnetic field and/or a toggling sequence of the static magnetic field to attempt to detect if an access code is encoded within a toggling sequence of the static magnetic field.

Accordingly, as will be described in more detail below, the user may press and hold INCREASE button 804 for a certain period of time (e.g., 20 seconds) in order to send a toggling sequence that, first, causes device 100 to remain in the waking mode while, second, a valid access code is provided to wake device 100 and cause device 100 to begin a manual stimulation session. In certain examples, only after the access code has been provided in this way may device 100 listen for and/or respond to any further commands sent by external controller 800. In other words, if a proper access code is not provided by external controller 800 in this way, device 100 may remain asleep (e.g., in shelf mode, in sleep mode waiting for the next scheduled therapy session, etc.) and may be unresponsive to commands sent by external controller 800. As such, it may be nearly impossible for static magnetic fields around the patient to inadvertently control device 100, even if a toggling sequence with a valid multi-bit command were to be inadvertently sent.

When device 100 receives a valid access code, device 100 may switch from the shelf mode or the sleep mode into a manual session mode where a manual stimulation session may be performed and in which device 100 may listen for and respond to additional commands. The manual session mode may also be referred to as a "programming mode" because, in manual session mode, the user may press INCREASE button 804 to increase a parameter (e.g., an amplitude) of the stimulation, press DECREASE button 806 to decrease the parameter of the stimulation, press STOP button 808 to stop the manual stimulation session and leave the programming mode (e.g., returning to sleep mode), and/or to otherwise receive commands and/or to be controlled or programmed. Specific examples of commands that may be sent and modes that may be traversed by device 100 will be provided below.

After the access code has been provided and device 100 is in the programming mode, external controller 800 and/or device 100 may implement features to make wireless communication between external controller 800 and device 100 convenient for the user to understand and control. For example, while it may take several seconds for external controller 800 to send a single command to device 100, external controller 800 may be configured to send an entire command with a single button press (e.g., a button press with a duration much shorter than the corresponding command will take to send). For example, sending a command to decrease the amplitude of stimulation may take three seconds for external controller 800 to send, but external controller 800 may send the entire command based on detecting a tap of DECREASE button 806 that takes only 200 milliseconds. Moreover, device 100 may only perform a particular command once in a given period of time (e.g., a debounce period of 5 seconds). Thus, for example, if the user presses DECREASE button 806 two or three times in succession (e.g., faster than a command associated with the button can be transmitted to device 100 by external controller 800), external controller 800 may only send one command and/or device 100 may only receive and perform one associated action. Thus, in order to cause device 100 to perform multiple actions associated with DECREASE button 806, the user may press DECREASE button 806 multiple times with at least the period of time (e.g., 5 seconds) elapsing between each press of the button.

To facilitate the user in performing the wireless communication with device 100 using external controller 800, TRANSMIT indicator LED 808 may light up in any suitable way (e.g., solid, blinking, etc.) to indicate that a downlink signal (e.g., a toggling sequence generated by external controller 800) is being transmitted to device 100. As such, the user may see when an entire command has been sent and when a new command may be input for transmission to the device. Additionally, CHARGE indicator LED 810 may light up in any suitable way when a battery in external controller 800 is being charged. For example, CHARGE indicator LED 810 may light up as one color (e.g., red) when the battery is charging, and may light up as another color (e.g., green) when the battery is fully charged.

External controller 800 is described and illustrated as one example of an external controller that may be used to perform wireless communication with a subcutaneous medical device such as device 100. However, it will be understood that various other types of external controllers (e.g., with more or fewer buttons or indicator LEDs, implementing fewer or additional commands corresponding to respective subcutaneous medical devices being controlled, etc.) may be used in particular implementations. Additionally, it will be understood that additional commands not explicitly described above (e.g., commands for transitioning back to shelf mode, advanced commands, etc.) may be implemented by external controller 800 and may be communicated to device 100 using the same principles described above. In some examples, commands may overload buttons 802-806 such that the commands may be sent when multiple buttons are pressed at once, when buttons are pressed in a particular sequence and/or with particular timing, or the like. Specific additional commands and examples of controlling device 100 will be given below.

On the right side of FIG. 8, the internal block diagram of external controller 800 is shown to include control circuitry 812, a battery 814, an electromagnet 816, and a pickup coil array 818, all of which may be communicatively coupled with one another and/or with other components not explicitly shown in order to perform the operations described above. Additionally, as illustrated by the internal block diagram of device 100 on the right side of FIG. 8, device 100 may include battery 606 (described above) as well as components (e.g., components 604, described above) including, for example, a coil-less magnetic field sensor 820, a pickup coil 822, and control circuitry 824. In operation, components within external controller 800 and/or device 100 may interoperate to generate a wireless downlink signal 826 and/or a wireless uplink signal 828 by which external controller 800 and device 100 may wirelessly communicate using a digital wireless communication protocol, as will be described in more detail below. Each of the exemplary internal components of external controller 800 and device 100 shown in FIG. 8 will now be described, as well as the uplink and downlink signals that the components transmit.

Control circuitry 812 of external controller 800 may include any hardware circuitry (e.g., specialized hardware circuitry, microcontroller circuitry, etc.) and/or software, firmware, or other instructions for performing the operations described herein. For example, control circuitry 812 may include circuitry for detecting that one of buttons 802-806 has been pressed and/or for determining a duration for how long the button is pressed, for directing one of indicator LEDs 808 or 810 to light up, for detecting that pickup coil array 818 has detected uplink signal 828, for directing electromagnet 816 to be energized and/or de-energized to generate a particular toggling sequence of a static magnetic field, and/or for performing any other operation of external controller 800 as may serve a particular implementation.

Battery 814 may provide electrical power for control circuitry 812, electromagnet 816, and/or other components of external controller 800. Battery 814 may be user-replaceable and/or may be rechargeable (e.g., by plugging in a charging cable sold with external controller 800).

Electromagnet 816 may be used to generate a toggling sequence between a presence and an absence of a static magnetic field representative of a digital data stream according to a digital wireless communication protocol. For example, electromagnet 816 may create the presence of the static magnetic field when electromagnet 816 is energized (i.e., when current is flowing through electromagnet 816), and may create the absence of the static magnetic field when electromagnet 816 is de-energized (i.e., when current flow through electromagnet 816 ceases). Accordingly, control circuitry 812 may use electromagnet 816 to create the presence and absence of the static magnetic field with a timing that, when detected and interpreted by device 100 in accordance with the digital wireless communication protocol, will represent a digital data stream encoding one or more commands (e.g., multi-bit commands) associated with commands indicated by the user of external controller 800 (e.g., by pushing one or more of buttons 802-806). Exemplary digital wireless communication protocols will be described and illustrated below.

By using electromagnet 816 to generate the toggling sequence between the presence and absence of the static magnetic field as described above, external controller 800 may wirelessly transmit a downlink signal 826 to device 100 through the skin of the patient, as shown in FIG. 8. Device 100 may receive and process downlink signal 826 and perform one or more actions associated with one or more commands encoded in downlink signal 826.

Coil-less magnetic field sensor 820 may be used to detect downlink signal 826. Advantageously, coil-less magnetic field sensor 820 may be extremely small and/or may use extremely little power in order to fit within strict size and power budget constraints of device 100. As opposed to conventional wireless communication transceivers, coil-less magnetic field sensor 820 may not be associated with any antenna coil or other type of antenna for receiving electromagnetic signals. Instead, coil-less magnetic field sensor 820 may include or be implemented by an AMR sensor, a Hall effect sensor, a Reed switch, or another type of coil-less magnetic field sensor as may serve a particular implementation. AMR sensors and Hall effect sensors represent examples of solid-state electronic sensors for detecting static magnetic fields, while Reed switches represent an example of an electromechanical type of device for detecting such fields. Regardless of the principle underlying the detection of the static magnetic fields in any of these sensors, however, each type of coil-less magnetic field sensor may be small and low power to fit within the size and power budgets of device 100. In certain examples, other types of coil-less magnetic field sensors may also be used in addition or as alternatives to the examples described above.

Control circuitry 824 of device 100 may be powered by battery 606 (described above) and, like control circuitry 812 of external controller 800, may include any hardware circuitry (e.g., specialized hardware circuitry, microcontroller circuitry, etc.) and/or software, firmware, or other instructions for performing the operations described herein. For example, control circuitry 824 may include circuitry for receiving an electrical signal output by coil-less magnetic field sensor 820 that is representative of the toggling sequence being detected by coil-less magnetic field sensor 820. Control circuitry 824 may further include hardware and/or software logic for interpreting the toggling sequence as a digital data stream, for identifying one or more multi-bit commands encoded within the digital data stream, and/or for performing actions associated with the multi-bit commands that may be identified. For example, control circuitry 824 may interpret the toggling sequence according to a digital wireless communication protocol such as one of the digital wireless communication protocols described below.

In some examples, control circuitry 824 may cause pickup coil 822 to indicate an acknowledgment ("ACK") response and/or a non-acknowledgement ("NACK") response to external controller 800 over uplink signal 828. For example, pickup coil 822 may be a small electromagnetic coil that senses when a boost converter within device 100 (not explicitly shown) is cycled off and back on based on a control signal sent from control circuitry 824. Pickup coil 822 may generate a small pulse that, when detected, filtered, and/or amplified by one or more pickup coils within pickup coil array 818 of external controller 800, may provide communication from device 100 to external controller 800. In some examples, communication sent by device 100 over uplink signal 828 may be simple and/or binary data. For example, a single pulse may be sent over uplink signal 828 to indicate that device 100 identified a multi-bit command encoded within a digital data stream sent by external controller 800, or that device 100 performed an action associated with such a multi-bit command. In other examples, communications sent over uplink signal 828 may be more complex. For example, wireless communication over uplink signal 828 may use a digital wireless communication protocol the same as or similar to digital wireless communication protocols described herein to send multi-bit messages to external controller 800 as may serve a particular implementation. Pickup coil array 818 may include one or more pickup coils configured to sense pulses generated by pickup coil 822 on uplink signal 828 and may communicate with control circuitry 812 to indicate that such pulses were sensed so that control circuitry 812 may respond accordingly (e.g., by using an indicator LED to indicate to the user a command was successfully sent or performed and/or that a next command may be sent, by sending a next command in a buffer, etc.).

Digital wireless communication protocols that may be used by external controller 800 and/or device 100 to perform wireless communications will now be described. Due to the nature of coil-less static magnetic field sensors, digital wireless communication protocols designed to work with static magnetic fields and/or coil-less static magnetic field sensors, may account for certain characteristics that may not need to be accounted for in the design of conventional digital wireless communication protocols (e.g., protocols using electromagnetic signals transmitted and received using antennas). For example, certain static magnetic field sensors may be configured to detect static magnetic fields only at discrete intervals, rather than continuously. For example, coil-less magnetic field sensor 820 may only detect changes to a presence or absence of a static magnetic field once during a particular period of time (e.g., 60 milliseconds ("ms")). In some examples, the sampling time of the coil-less magnetic field sensor may not be strictly periodic, but may need to be treated asynchronously. For example, rather than sampling the static magnetic field at a predictable moment every particular period of time (e.g., every 60 ms), coil-less magnetic field sensor 820 may only be guaranteed to sample within the particular period of time, but not at any particular moment within the particular period of time.

Figure 9:
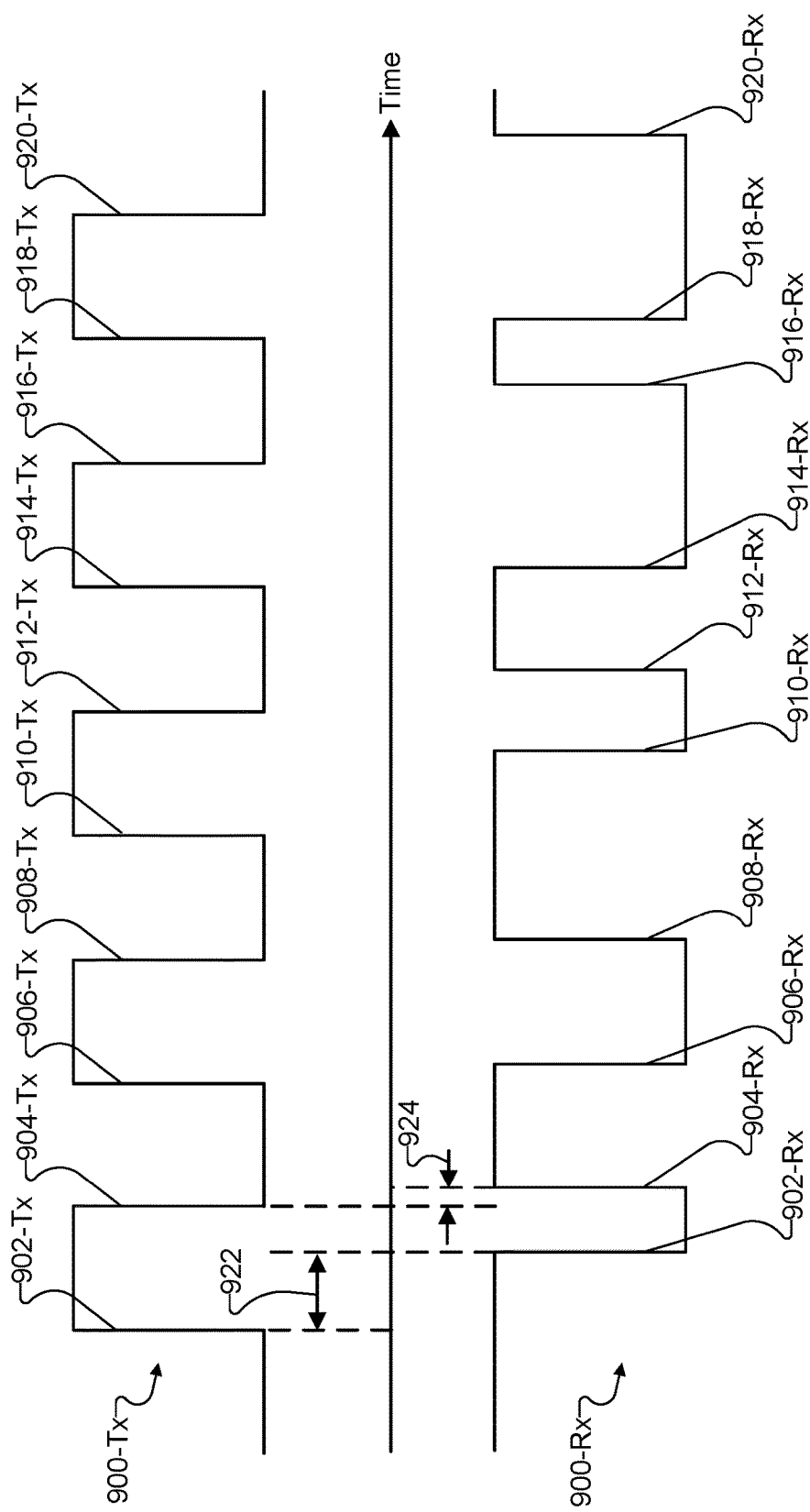
FIG. 9 illustrates exemplary timing waveform diagrams of an externally-generated static magnetic field and detection of the externally-generated static magnetic field by a coil-less magnetic field sensor included within the subcutaneous medical device illustrated in FIG. 1 according to principles described herein.

To illustrate, FIG. 9 shows exemplary timing waveform diagrams of an externally-generated static magnetic field and detection of the externally-generated static magnetic field by a coil-less magnetic field sensor included within device 100. More specifically, FIG. 9 illustrates a toggling sequence 900-Tx representative of a signal (e.g., downlink signal 826) transmitted by external controller 800 and, on the same timeline, a corresponding toggling sequence 900-Rx representative of the same signal as the signal is received by device 100. In particular, toggling sequence 900-Tx illustrates a presence of a static magnetic field created by electromagnet 816 when electromagnet 816 is energized (represented by toggling sequence 900-Tx being HIGH) and an absence of the static magnetic field created by electromagnet 816 when electromagnet 816 is de-energized (represented by toggling sequence 900-Tx being LOW). Similarly, toggling sequence 900-Rx illustrates the corresponding timing of coil-less magnetic field sensor 820 detecting the static magnetic field whose presence and absence electromagnet 816 is creating. In particular, toggling sequence 900-Rx illustrates the presence of the static magnetic field detected by coil-less magnetic field sensor 820 (represented by toggling sequence 900-Rx being LOW) and the absence of the static magnetic field detected by coil-less magnetic field sensor 820 (represented by toggling sequence 900-Rx being HIGH).

Thus, for example, each edge of toggling sequence 900-Tx (e.g., edges 902-Tx, 904-Tx, 906-Tx, 908-Tx, 910-Tx, 912-Tx, 914-Tx, 916-Tx, 918-Tx, and 920-Tx) represents a change to (i.e., a toggling of) the static magnetic field. Specifically, rising edges 902-Tx, 906-Tx, 910-Tx, 914-Tx, and 918-Tx each represent an energizing of electromagnet 816 causing the presence of the static magnetic field to be created. Meanwhile, falling edges 904-Tx, 908-Tx, 912-Tx, 916-Tx, and 920-Tx each represent a de-energizing of electromagnet 816 causing the absence of the static magnetic field to be created.

Each change to (i.e., toggling of) the static magnetic field is detected by coil-less magnetic field sensor 820, albeit not necessarily with consistent or predictable timing. To illustrate, each edge of toggling sequence 900-Rx (e.g., edges 902-Rx, 904-Rx, 906-Rx, 908-Rx, 910-Rx, 912-Rx, 914-Rx, 916-Rx, 918-Rx, and 920-Rx) represents a corresponding detection of the change to the static magnetic field represented by the similarly numbered edge of toggling sequence 900-Tx. For example, edge 902-Rx represents a detection, by coil-less magnetic field sensor 820, of the static magnetic field generated by electromagnet 816 being energized at edge 902-Tx. Similarly, edge 904-Rx represents a detection that the static magnetic field disappears when electromagnet 816 is de-energized at edge 904-Tx.

As shown, there may not be a consistent temporal relationship between edges of toggling sequence 900-Tx and corresponding edges of toggling sequence 900-Rx. For example, even though each edge of toggling sequence 900-Tx may come at regular intervals, each corresponding edge of toggling sequence 900-Rx may occur at irregular intervals within a particular period of time (e.g., 60 ms) after the static magnetic field actually changed. For example, as shown by interval 922, a relatively long interval may occur after the presence of the static magnetic field is created at edge 902-Tx and before the presence is detected at edge 902-Rx, while, as shown by interval 924, a relatively short interval may occur after the absence of the static magnetic field is created at edge 904-Tx and before the absence is detected at edge 904-Rx. As shown, other intervals (not explicitly labeled) may each occur with similar inconsistency and/or unpredictability, although interval 922, interval 924, and the other intervals not explicitly labeled may each last less than the particular period of time (e.g., less than 60 ms). Accordingly, as described above, a digital wireless communication protocol utilizing static magnetic fields and a coil-less magnetic field sensor may account for the possibility that a regular periodic signal (e.g., such as toggling sequence 900-Tx) that is transmitted to device 100 may be received as an irregular signal (e.g., such as toggling sequence 900-Rx).

Figure 10:
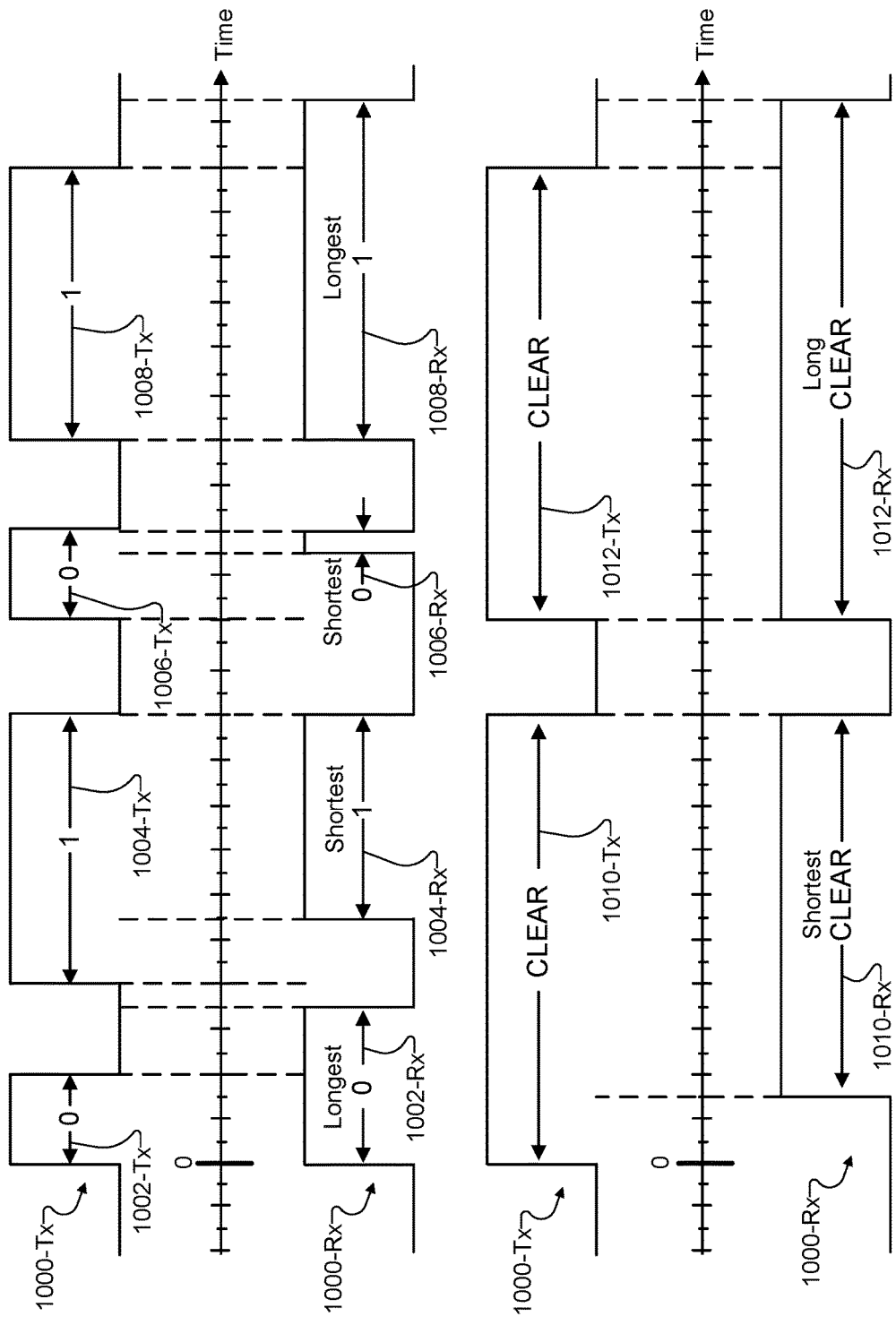
FIG. 10 shows exemplary timing waveform diagrams that illustrate particular aspects of an exemplary digital wireless communication protocol according to principles described herein.

FIG. 10 shows exemplary timing waveform diagrams that illustrate particular aspects of one exemplary digital wireless communication protocol that may account for the characteristics of static magnetic fields and/or coil-less magnetic field sensors to facilitate wireless communication between external controller 800 and device 100. Specifically, FIG. 10 illustrates an edge-to-edge timing duration protocol in which data bits are encoded within the durations between edges of a toggling sequence 1000-Tx. Like toggling sequence 900-Tx, described above, toggling sequence 1000-Tx may be generated by external controller 800 and, more particularly, by energizing and de-energizing electromagnet 816 at particular times to generate toggling sequence 1000-Tx. A corresponding toggling sequence 1000-Rx is illustrated beneath toggling sequence 1000-Tx to represent the timing with which device 100 (e.g., coil-less magnetic field sensor 820) may detect toggling sequence 1000-Tx. More specifically, toggling sequence 1000-Rx illustrates the corner cases for the best and worst case delay times that may occur between an edge of toggling sequence 1000-Tx and an edge of toggling sequence 1000-Rx. For example, in one implementation, a best case delay may be 0 ms (i.e., an edge of toggling sequence 1000-Rx may occur simultaneously with the corresponding edge of toggling sequence 1000-Tx), while a worst case delay may be the entire duration of the particular time period (i.e., an edge of toggling sequence 1000-Rx may be delayed by, for example, a full 60 ms time period after the corresponding edge of toggling sequence 1000-Tx).

In order to illustrate corresponding edges and transmitted data bits as clearly and conveniently as possible in FIG. 10, rising edges on toggling sequence 1000-Tx are shown to correspond to rising edges on toggling sequence 1000-Rx, while falling edges on toggling sequence 1000-Tx are similarly shown to correspond to falling edges of toggling sequence 1000-Rx. Additionally, each bit (both during transmission and when received) is labeled as beginning on a rising edge and ending on a subsequent falling edge, with no data labeled as being transmitted or received between falling edges and subsequent rising edges. However, it will be understood that, in certain implementations (e.g., as illustrated in FIG. 9), the respective polarities of toggling sequences 1000-*Tx* and 1000-*Rx* may be inverted such that rising edges in toggling sequence 1000-*Tx* correspond with falling edges in toggling sequence 1000-*Rx*, and vice versa. Additionally, it will be understood that, in certain implementations, data may be encoded in durations between falling edges and subsequent rising edges as an alternative to or in addition to being encoded in the durations between rising edges and subsequent falling edges, as shown and labeled in FIG. 10

The digital wireless communication protocol of FIG. 10 may specify, as a first binary value, a first range for a duration between changes to the externally-generated static magnetic field in toggling sequence 1000-*Tx*. For example, the first binary value may be a binary zero and the first range for the duration between the changes to the externally-generated static magnetic field may be a range from 0 ms up to a first number of milliseconds. To account for the delay of the particular period of delay time associated with coil-less magnetic field sensor 820, the first number of milliseconds at the upper end of the first range may be slightly longer than twice the particular period of delay time (e.g., to provide a margin of error or guard band). For example, if the particular period of delay time (i.e., the delay illustrated in FIG. 9) is 60 ms, the first range may be from 0 ms up to 160 ms (e.g., two times longer than 80 ms, or twice as long as 60 ms plus 20 ms of guard band).

The digital wireless communication protocol may further specify, as a second binary value, a second range for a duration between changes to the externally-generated static magnetic field in toggling sequence 1000-*Tx*. For example, the second binary value may be a binary one and the second range for the duration between the changes to the externally-generated static magnetic field may be a range from the first number of milliseconds up to a second number of milliseconds (i.e., a number greater than the first number of milliseconds). To account for the delay of the particular period of delay time associated with coil-less magnetic field sensor 820, the second number of milliseconds at the upper end of the second range may be twice as long as the first number of milliseconds (e.g., into which the margin of error or guard band accounting for the delay time is already incorporated). For example, if the particular period of delay time is 60 ms and the first range is from 0 ms up to 160 ms, the second range may be from 160 ms up to 320 ms (e.g., twice the duration of 160 ms).

Additionally, as mentioned above, and as will be described in more detail below, device 100 may capture data (e.g., one or more instances of the binary zero and of the binary one included within the digital data stream represented by toggling sequence 1000-*Tx*) using one or more FIFO buffers. As such, in certain implementations, the digital wireless communication protocol may specify, as a reset value to clear the FIFO buffer (i.e., as a CLEAR_FIFO bit), a third range for the duration between the changes to the externally-generated static magnetic field in toggling sequence 1000-*Tx*. For example, the third range may extend from the second number of milliseconds (e.g., 160 ms in the example described above) up to an unlimited number of milliseconds.

In FIG. 10, toggling sequence 1000-*Rx* illustrates corner cases for each type of bit described above (e.g., zero bits, one bits, and FIFO_CLEAR bits) according to best-case and worst-case delay times that may occur between an edge of toggling sequence 1000-*Tx* and a corresponding edge of toggling sequence 1000-*Rx*. Specifically, a zero bit 1002-*Tx* encoded on toggling sequence 1000-*Tx* for transmission to device 100 may be received by device 100 as a longest zero bit 1002-*Rx*, a one bit 1004-*Tx* encoded on toggling sequence 1000-*Tx* may be received by device 100 as a shortest one bit 1004-*Rx*, a zero bit 1006-*Tx* encoded on toggling sequence 1000-*Tx* may be received by device 100 as a shortest zero bit 1006-*Rx*, a one bit 1008-*Tx* encoded on toggling sequence 1000-*Tx* may be received by device 100 as a longest one bit 1008-*Rx*, a CLEAR_FIFO bit 1010-*Tx* encoded on toggling sequence 1000-*Tx* may be received by device 100 as a shortest CLEAR_FIFO bit 1010-*Rx*, and a CLEAR_FIFO bit 1012-*Tx* encoded on toggling sequence 1000-*Tx* may be received by device 100 as a long CLEAR_FIFO bit 1012-*Rx*. It is noted that, while long CLEAR_FIFO bit 1012-*Rx* is longer than shortest CLEAR_FIFO bit 1010-*Rx*, there may be no limit to how long a CLEAR_FIFO bit may be and, thus, no such thing as a "longest" CLEAR_FIFO bit.

As shown, the durations at which each type of bit are encoded on toggling sequence 1000-*Tx* for transmission may be consistent. For example, zero bit 1002-*Tx* and zero bit 1006-*Tx* may both be encoded on toggling sequence 1000-*Tx* with a duration of the particular time period plus the guard band. Thus, for instance, using the example described above where the particular time period (i.e., the maximum delay time period of coil-less magnetic field sensor 820 illustrated by FIG. 9) is 60 ms, external controller 800 may energize electromagnet 816 for 80 ms (i.e., 60 ms plus 20 ms of guard band) to represent zero bits 1002-*Tx* and 1006-*Tx* before toggling (i.e., de-energizing) electromagnet 816 to begin encoding the next respective bits. Thus, in this example, each tick mark on the time axis may represent 20 ms.

Similarly, one bit 1004-*Tx* and one bit 1008-*Tx* may both be encoded on toggling sequence 1000-*Tx* as three times the duration of a zero bit (i.e., the particular time period plus the guard band). Thus, for instance, following the same numerical example above where the zero bit is encoded as an 80 ms duration, external controller 800 may energize electromagnet 816 for 240 ms (i.e., three times 80 ms) to represent one bits 1004-*Tx* and 1008-*Tx* before toggling (i.e., de-energizing) electromagnet 816 to begin encoding the next respective bits. Moreover, CLEAR_FIFO bit 1010-*Tx* and CLEAR_FIFO bit 1012-*Tx* may both be encoded on toggling sequence 1000-*Tx* as five times the duration of the duration of a zero bit (i.e., the particular time period plus the guard band). Accordingly, in the running numerical example described above where the zero bit is encoded as an 80 ms duration, external controller 800 may energize electromagnet 816 for 400 ms (i.e., five time 80 ms) to represent CLEAR_FIFO bits 1010-*Tx* and 1012-*Tx*. It is noted that, in some examples, (e.g., between distinct commands a user indicates to send using external controller 800), a CLEAR_FIFO bit may be arbitrarily long (e.g., several seconds, minutes, or more).

It will be understood that the time periods and the relationships between the time periods described above (e.g., based on the 60 ms delay time and the 20 ms guard band) are exemplary only and that other time periods and/or relationships between time periods may be used as may serve a particular implementation. However, with that understanding, it may be instructive to examine FIG. 10 using the specific numerical examples referred to above. Specifically, if it is assumed that each tick mark on the time axis represents 20 ms of time, it may be seen that external controller 800 begins sending zero bit 1002-*Tx* at 0 ms at finishes sending zero bit 1002-*Tx* at 80 ms. In response, longest zero bit 1002-*Rx* shows the longest possible zero bit that may be received for a transmitted 80 ms zero bit. Specifically, longest zero bit 1002-*Rx* shows that a minimum delay (i.e., 0 ms) occurs between the respective first edges of zero bit 1002 (i.e., zero bits 1002-*Tx* and 1002-*Rx*) while a maximum delay (i.e., 60 ms) occurs between the respective second edges of zero bit 1002. Accordingly, as shown, the longest possible zero bit is 140 ms, giving a 20 ms margin of error before reaching the top of the first range defining zero bits at 160 ms.

At the other extreme, the shortest possible zero bit is illustrated by shortest zero bit 1006-*Rx*, which occurs when a maximum delay (i.e., 60 ms) occurs between respective first edges of zero bit 1006 (i.e., zero bits 1006-*Tx* and 1006-*Rx*) while minimum delay (i.e., 0 ms) occurs between the respective second edges of zero bit 1006. As shown, the shortest possible zero bit is 20 ms, again giving a 20 ms margin of error before reaching the bottom of the first range at 0 ms.

The same idea is illustrated by shortest one bit 1004 (i.e., one bits 1004-*Tx* and 1004-*Rx*) and by longest one bit 1008 (i.e., one bits 1008-*Tx* and 1008-*Rx*). Specifically, shortest one bit 1004 has a maximum delay of 60 ms between the first edges and minimum delay of 0 ms between the second edges to generate shortest one bit 1004-*Rx* with a duration of 180 ms (i.e., leaving 20 ms of guard band with the bottom end of the second range defining one bits (160 ms)). Conversely, longest one bit 1008 has a minimum delay of 0 ms between the first edges and a maximum delay of 60 ms between the second edges to generate longest one bit 1008-*Rx* with a duration of 300 ms (i.e., leaving 20 ms of guard band with the top end of the second range defining one bits (320 ms)).

The same is true also for shortest CLEAR_FIFO bit 1010 (i.e. CLEAR_FIFO bits 1010-*Tx* and 1010-*Rx*) and long CLEAR_FIFO bit 1012 (i.e., CLEAR_FIFO bits 1012-*Tx* and 1012-*Rx*). That is, shortest CLEAR_FIFO bit 1010 has a maximum delay of 60 ms between the first edges and minimum delay of 0 ms between the second edges to generate shortest CLEAR_FIFO bit 1010-*Rx* with a duration of 340 ms (i.e., leaving 20 ms of guard band with the bottom end of the third range defining CLEAR_FIFO bits (320 ms)). Conversely, long CLEAR_FIFO bit 1012 has a minimum delay of 0 ms between the first edges and a maximum delay of 60 ms between the second edges to generate longest CLEAR_FIFO bit 1012-*Rx* with a duration of 460 ms.

Accordingly, as illustrated in FIG. 10, zero bits, one bits, and CLEAR_FIFO bits may be encoded by durations between changes to a static magnetic field and may be differentiated from one another even accounting for worst case scenarios in delay times for a coil-less magnetic field sensor detecting the static magnetic fields. In other words, because the respective first, second, and third ranges defining the durations for zero bits, one bits, and CLEAR_FIFO bits are non-overlapping in the digital wireless communication protocol of FIG. 10, device 100 may interpret a toggling sequence (e.g., toggling sequence 1000-*Rx*) as a digital data stream including zero bits, one bits, and/or CLEAR_FIFO bits without risk of interpreting unintended bits in spite of unpredictable delays in detecting the static magnetic field by coil-less magnetic field sensor 820.

Figure 11:
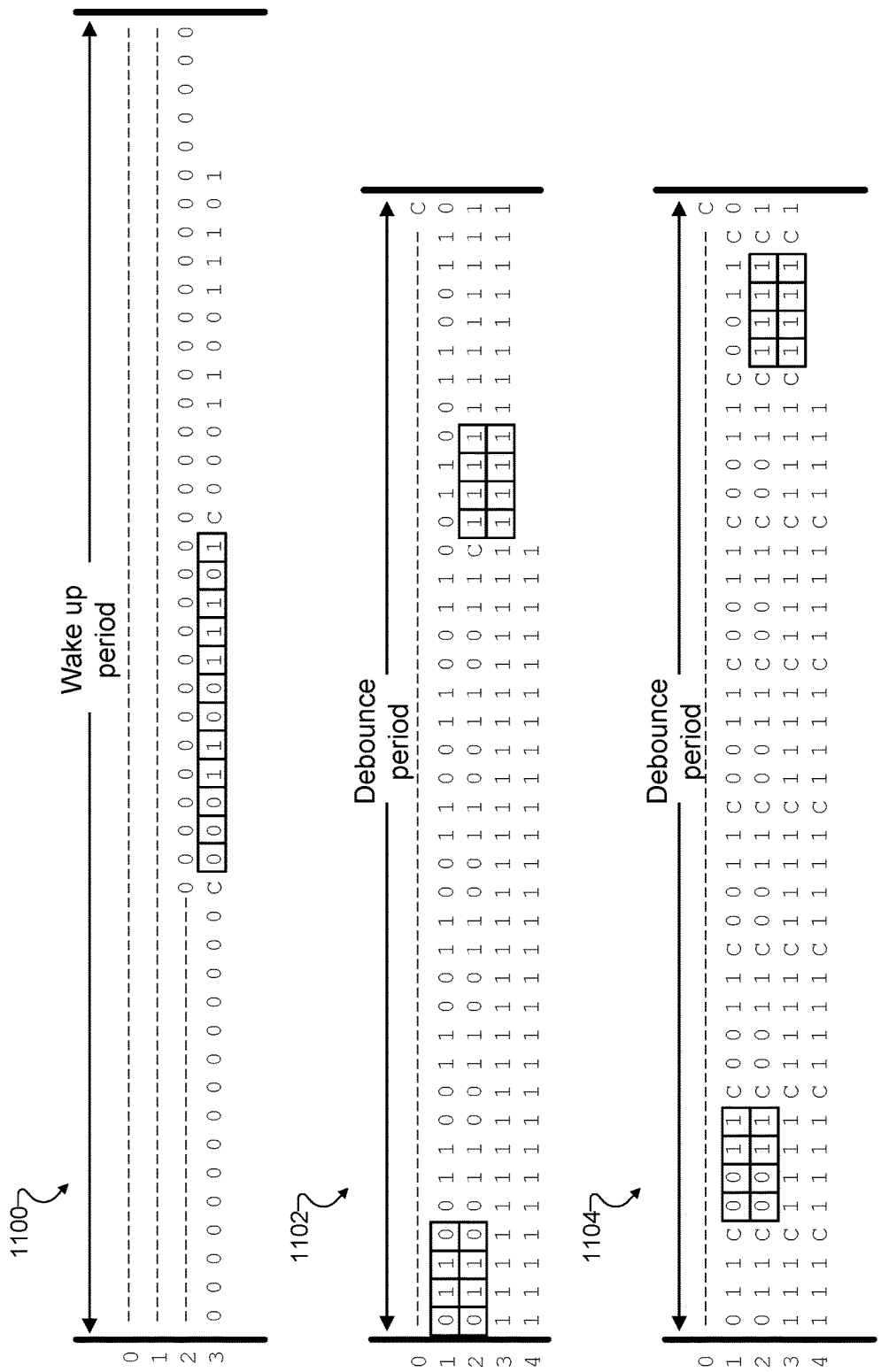
FIG. 11 shows exemplary bit sequences that illustrate particular aspects of the digital wireless communication protocol of FIG. 10 according to principles described herein.

Using the digital wireless communication protocol described above with respect to FIG. 10, external controller 800 and device 100 may communicate various bit sequences representative of various types of commands in various different ways. To illustrate, FIG. 11 shows exemplary bit sequences that illustrate particular aspects of the digital wireless communication protocol of FIG. 10. For example, bit sequence 1100 illustrates particular aspects of waking device 100 (e.g., in order to send commands to device 100), and bit sequences 1102 and 1104 illustrate particular aspects of alternative ways that device 100 may determine the commencement of repeated instances of multi-bit commands encoded in a digital data stream.

As described above, device 100 may operate in a low power operating mode (e.g., sleep mode, shelf mode, etc.) in which device 100 ignores toggling sequences between the presence and the absence of the externally-generated static magnetic field most of the time. Then, for a first amount of time (e.g., 160 ms) once every period of a second amount of time (e.g., once every 10 seconds), device 100 may automatically and temporarily switch from operating in the low power operating mode in which device 100 ignores the toggling sequences, to a waking operating mode in which device 100 attempts to detect the initial toggling sequence. The first and second amounts of time may be configured to conserve battery life by allowing device 100 to spend significantly more time in the low power mode than in the waking operating mode. For example, the second amount of time may be at least ten times larger than the first amount of time.

To illustrate, bit sequence 1100 shows approximate wake up periods with bold lines in between which the transmitted bits of bit sequence 1100 are shown. For example, as described above, device 100 may stay in the low power mode most of the time (i.e., between the bold lines) but may briefly (e.g., for the first amount of time) switch to the waking operating mode to attempt to detect a static magnetic field and/or an initial toggling sequence once every so often (e.g., every second amount of time). Thus, the second amount of time ("wake up period") may be approximately represented by the bold lines such that each row of bit sequence 1100 may take an amount of time approximately equal to the wake up period to transmit, and the waking operating mode may be briefly switched to at the beginning of each row. It will be understood that the timing illustrated in FIG. 11 is for illustrative purposes only and is not drawn to scale. For example, since different bits take different amounts of time to send using the digital wireless communication protocol of FIG. 10, each row of bit sequences 1100, 1102, and 1104 may actually take different amounts of time to transmit.

As illustrated by bit sequence 1100, device 100 may check at the beginning of rows 0, 1, and 2 to see if a static magnetic field and/or a toggling sequence may be detected, and may return to a low power mode (e.g., shelf mode, sleep mode, etc.) upon determining that no such field or toggling sequence is detectable. However, if, as described above, a user holds the INCREASE button for at least an entire duration of the wake up period (i.e., thereby sending an initial toggling sequence representative of a stream of zero bits for at least one whole row), device 100 may detect the magnetic field and the initial toggling sequence (i.e., the repeated zero bits in row 2) upon checking at the beginning of row 3 of bit sequence 1100. In response, device 100 may begin to fill a FIFO buffer (e.g., a twelve-bit FIFO buffer) with incoming data represented by the toggling sequence. In other words, device 100 may detect (e.g., using coil-less magnetic field sensor 820) an initial toggling sequence between the presence and the absence of the externally-generated static magnetic field that is representative of an initial digital data stream according to the digital wireless communication protocol. Based on the detected initial toggling sequence and in accordance with the digital wireless communication protocol, device 100 may determine (e.g., after at least a full row of zero bits has been transmitted) that a predetermined access code (e.g., 0b000110011101 or 0x19D) is encoded within the initial digital data stream represented by the initial toggling sequence.

For example, as illustrated by the twelve consecutive boxes representing a twelve-bit FIFO, device 100 may determine that a valid access code is included within the initial toggling sequence. In response to the determining that the predetermined access code is encoded within the initial digital data stream, device 100 may allow access control to device 100. In other words, upon receiving the access code, device 100 may wake up and begin to listen for and/or accept multi-bit commands encoded within the digital data stream.

As shown in bit sequence 1102, once the access code has been provided such that device 100 is awake and listening for commands, the digital wireless communication protocol may specify a period lasting a particular amount of time (e.g., a "debounce period") in which the digital data stream contains only one multi-bit command, or, in other words, during which a particular command may only be performed once. For example, as described above with respect to FIG. 8, the debounce period may cause a command such as a decrease to a particular stimulation parameter to only be accepted once every 5 seconds, for example, even if a user presses the DECREASE button multiple times within the 5 second period.

In order to implement this, when external controller 800 detects a command indicated by a user (e.g., a four-bit command encoded as 0b0011 or 0x3), external controller 800 may be configured to repeatedly encode the multi-bit command within the digital data stream (e.g., repeating the multi-bit command at least once and possibly until a full duration of the debounce period has passed), and then to stop and wait for another command.

Thus, as illustrated by bit sequences 1102 and 1104, after a CLEAR_FIFO bit (i.e. 'C' at the end of row 0), external controller 800 may begin repeating the four-bit command (i.e., 0b0011) for one debounce period and the command may be received in a four-bit FIFO buffer illustrated by the four boxes in row 1.

Because a transmitted command may be repeated in this way (e.g., for error prevention, etc.), the identifying of the multi-bit command by device 100 may include determining the commencement of each repeated instance of the multi-bit command. For example, if device 100 is in a mode where a four-bit command is expected (e.g., device 100 is using a four-bit FIFO to examine the data or the bottom four bits of a twelve-bit FIFO buffer, for example), device 100 may be configured to identify a command of 0b0011 regardless of whether device 100 reads a digital data stream to be 0b001100110011 . . . , 0x011001100110 . . . , 0b110011001100 . . . , or 0b100110011001 . . . . Determining the commencement of each repeated instance may be performed in one of at least two ways, each illustrated by one of bit sequences 1102 and 1104.

For example, bit sequence 1102 illustrates that determining the commencement of each repeated instance may be performed by converting a plurality of bits representative of the multi-bit command and captured using the FIFO buffer into a minimum form. In other words, device 100 may detect an arbitrary four consecutive bits. For example, device 100 may detect the command as 0b0110, as illustrated by the four boxes on row 1 in bit sequence 1102. Device 100 may then convert the detected bits into a minimum form.

The minimum form of a binary sequence is the minimum number that the bits may represent when shifted around to every possible configuration. In other words, the minimum form may be obtained by shifting the bits of the sequence to move ones as far to the right as possible while zeros are moved to the left as far as possible.

For example, FIG. 12 illustrates an exemplary conversion table wherein 12-bit sequences are converted to a minimum form. On the left side of the table, a 12-bit sequence (i.e., 0b000000010011 or 0x013) is shown to be shifted into every possible order by shifting the sequence one bit to the left on each row. As shown on the right side of the table, however, regardless of how the bits are shifted, the minimum form is always the same (i.e., 0b000000010011 or 0x013). Thus, regardless of where a FIFO began to read a repeating pattern of 0b000000010011, if converted to the minimum form, the same command would be interpreted.

Returning to FIG. 11, bit sequence 1104 illustrates that, as an alternative to the method described in relation to bit sequence 1102, determining the commencement of each repeated instance may be performed by detecting, within the toggling sequence prior to each repeated instance of the multi-bit command, a CLEAR_FIFO bit (i.e., a reset value to clear the FIFO buffer). For example, as illustrated by bit sequence 1104, external controller 800 sends a CLEAR_FIFO bit immediately prior to each instance of the 0b0011 command such that device 100 merely has to detect the next four bits after any CLEAR_FIFO bit during the debounce period.

As further illustrated by bit sequences 1102 and 1104, the same command (e.g., 0b0011 in this example) may only be received again if the user sends the command again (e.g., or is still holding the button) after an entire debounce period has passed. Accordingly, as shown, because the user may be continuously holding down a button, the 0b001100110011 pattern continues for more than an entire debounce period after the command is identified in row 1 and is thus identified again as a separate command in row 2 (i.e., illustrated by the respective four consecutive boxes in row 2 of both bit sequences 1102 and 1104) only after the debounce period has passed.

Conversely, the debounce period may or may not need to pass prior to device 100 receiving a different command. For example, in both bit sequences 1102 and 1104, the command being transmitted changes, after a CLEAR_FIFO bit in the middle of row 2, from a command of 0b0011 to a command of 0b1111. As such, subsequent to the identifying of the first multi-bit command and based on the detected toggling sequence, device 100 may detect the CLEAR_FIFO bit (i.e., the reset value to clear the FIFO buffer), and, in response, may clear the FIFO buffer. Subsequently, device 100 may identify based on additional binary values represented in the toggling sequence subsequent to the CLEAR_FIFO bit, an additional multi-bit command encoded within the digital data stream and different from the first multi-bit command (i.e., 0b1111). In response to identifying the additional multi-bit command and subsequent to performing an action associated with the first multi-bit command, device 100 may perform an additional action associated with the additional multi-bit command.

While one digital wireless communication protocol has been described in detail above, it will be understood that other digital wireless communication protocols that similarly account for characteristics of static magnetic fields and/or coil-less magnetic field sensors (e.g., unpredictable delays associated with coil-less magnetic field sensors, etc.) may also be used in certain implementations. To illustrate, FIG. 13 shows exemplary timing waveform diagrams that illustrate particular aspects of an exemplary alternative digital wireless communication protocol that is based directly on signal levels (e.g., presence and absence of static magnetic fields) rather than on the duration between changes to the signal levels as described above in relation to the digital wireless communication protocol of FIG. 10.

Figure 13:
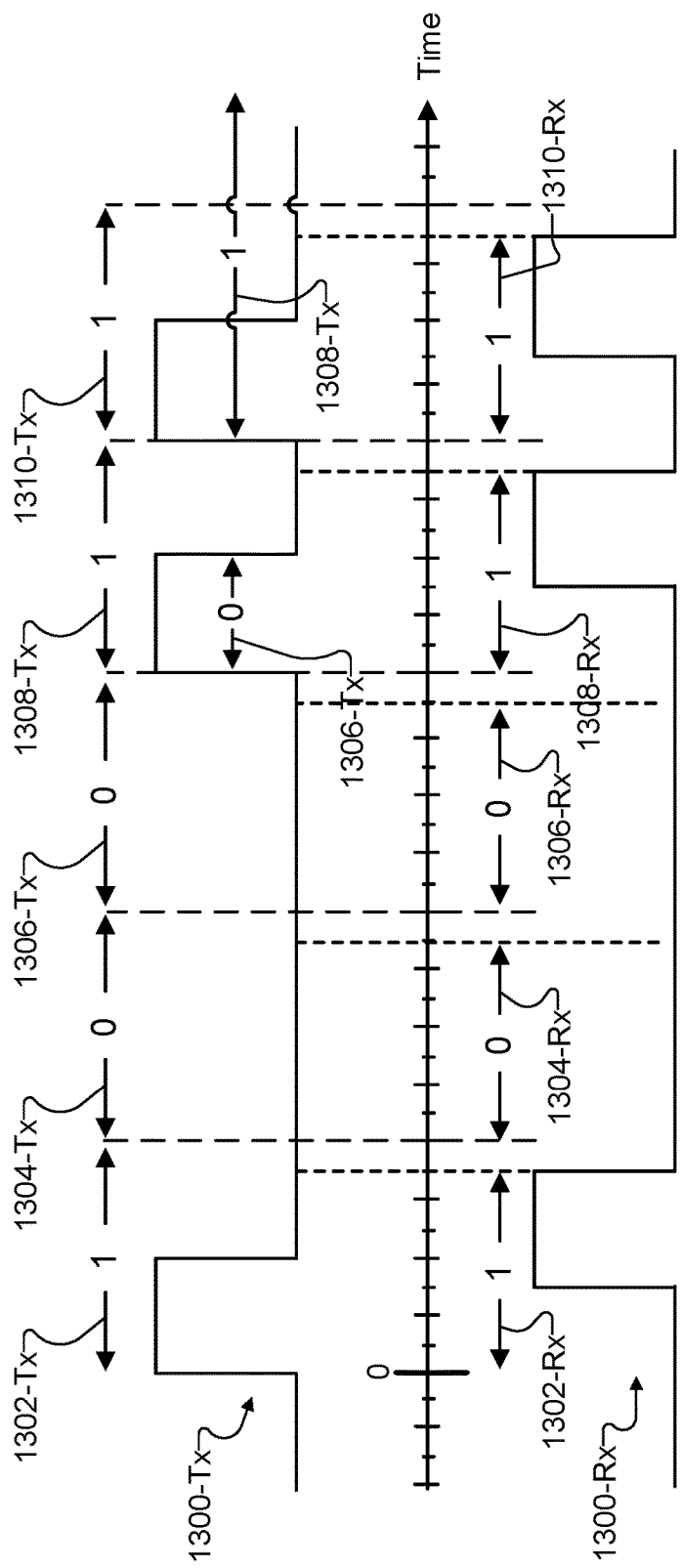
FIG. 13 illustrates exemplary timing waveform diagrams that illustrate particular aspects of an exemplary alternative digital wireless communication protocol according to principles described herein.

The digital wireless communication protocol of FIG. 13 may specify, as a first binary value (e.g., a binary zero), a first status of the externally-generated static magnetic field that is one of the presence and the absence of the externally-generated static magnetic field, and may specify, as a second binary value (e.g., a binary one), a second status of the externally-generated static magnetic field that is the other of the presence and the absence of the externally-generated static magnetic field opposite to the one specified for the first binary value. For example, as illustrated in FIG. 13, a binary zero may be represented by an absence of the externally-generated static magnetic field, while a binary one may be represented by a presence of the externally-generated static magnetic field. Accordingly, set bit periods (e.g., 160 ms) may be associated with each bit such that if a binary one is received, the binary one is guaranteed to fit within the bit period if transmitted during the first half of the bit period (e.g., the first 80 ms), and, if a timeout is received prior to the end of the bit period and no binary one has been detected, a binary zero may be assumed.

To illustrate, FIG. 13 shows a toggling sequence 1300-Tx in which five bits (i.e., 0b10011 from left to right) are encoded and transmitted by external controller 800. More specifically, bits 1302-Tx (a one bit), 1304-Tx (a zero bit), 1306-Tx (a zero bit), 1308-Tx (a one bit), and 1310-Tx (a one bit) are each encoded on toggling sequence 1300-Tx with one bit transmitted per bit period (illustrated by dotted lines). Beneath toggling sequence 1300-Tx but on the same time line, FIG. 13 shows a toggling sequence 1300-Rx in which the same five bits are decoded and received by device 100. In particular, bits 1302-Rx is decoded as a one bit, 1304-Rx is decoded as a zero bit, 1306-Rx is decoded as a zero bit, 1308-Rx is decoded as a one bit, and 1310-Rx is decoded as a one bit after a presence of an externally-generated static magnetic field is detected (in the case of the one bits) or after a timeout of a bit period is reached (in the case of the zero bits).

Various aspects of digital wireless communication protocols for encoding multi-bit commands within digital data streams represented by toggling sequences of externally-generated magnetic fields have been described. Additionally, as described above, once device 100 identifies a multi-bit command encoded within a digital data stream, device 100 may perform an action associated with the multi-bit command. In some examples, the action associated with the multi-bit command is to switch from one operating mode in a plurality of operating modes in which device 100 may operate to another operating mode in the plurality of operating modes. For example, the plurality of operating modes may include a shelf mode, a sleep mode, an automatic session mode, and a manual session mode.

Additionally, the digital wireless communication protocol may specify one or more basic multi-bit commands each defined by a first number of bits (e.g., four bits) and may further specify one or more advanced multi-bit commands each defined by a second number of bits greater than the first number of bits (e.g., twelve bits). As such, the plurality of operating modes may additionally include an advanced command mode in which the identifying of the multi-bit command includes identifying an advanced multi-bit command from the one or more advanced multi-bit commands defined by the second number of bits.

Figure 14:
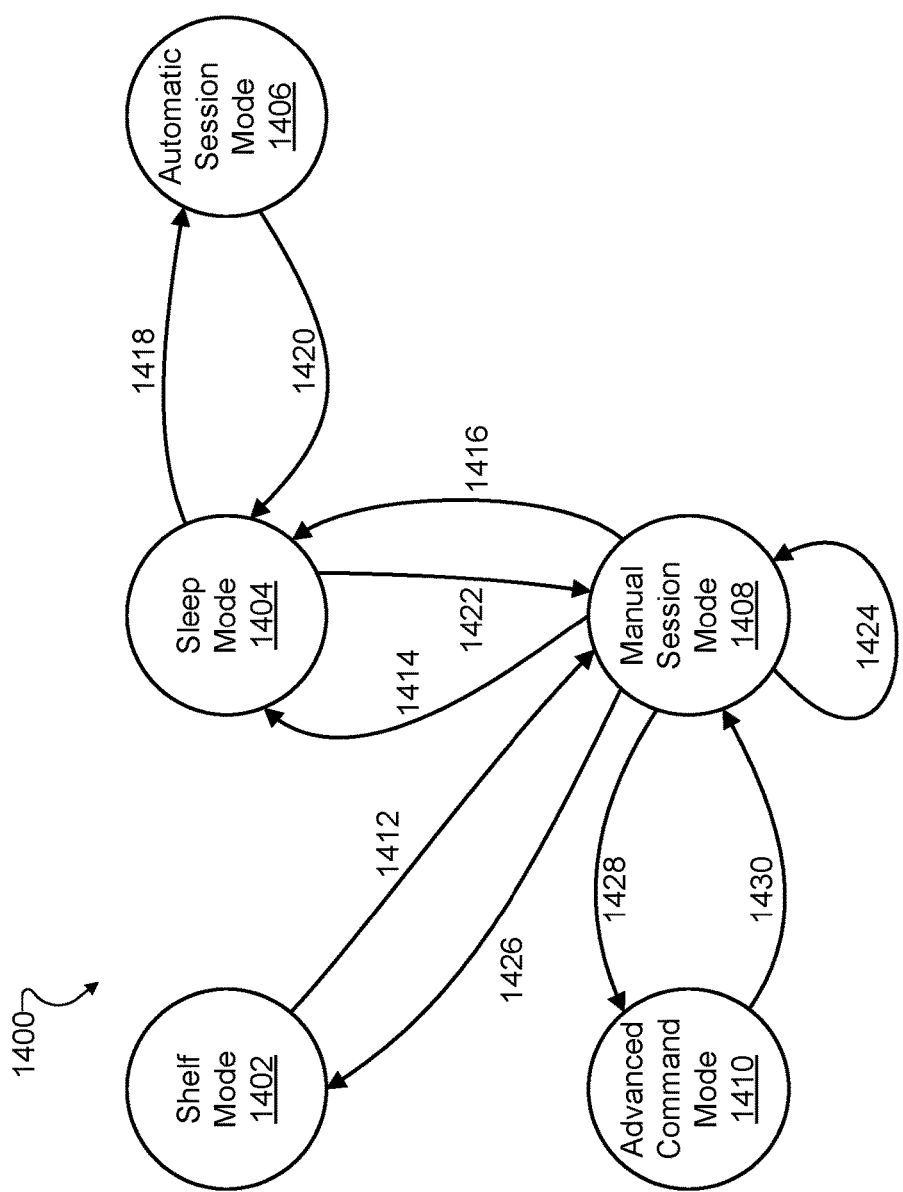
FIG. 14 illustrates an exemplary state diagram in accordance with which the subcutaneous medical device illustrated in FIG. 1 may be controlled according to principles described herein.

To illustrate, FIG. 14 shows an exemplary state diagram 1400 in accordance with which device 100 may be controlled. Specifically, state diagram 1400 illustrates various states or modes in which device 100 may operate and illustrates what may occur to cause device 100 to transition (i.e., switch) from operating in one mode to operating in another mode. As will be described below, in many examples, the action associated with a multi-bit command that device 100 performs may relate to transitioning from one mode to another.

As shown, state diagram 1400 includes a shelf mode 1402, a sleep mode 1404, an automatic session mode 1406, a manual session mode 1408, and an advanced command mode 1410. The modes shown and described in relation with state diagram 1400 may be particularly useful for a subcutaneous medical device that is a subcutaneous neuromodulation system including an EA device such as EA device 200, described above. However, it will be understood that additional, fewer, and/or different states may be used in various implementations of device 100, particularly in implementations that include different types of subcutaneous medical devices (i.e., other than EA devices). For example, certain implementations may include a power-on-reset mode that may transition to a lower power mode such as shelf mode 1402 or sleep mode 1404 depending on whether a therapy session (e.g., an electroacupuncture stimulation session) has been completely delivered. Each mode within state diagram 1400 and certain transitions between the respective modes will now be described.

After manufacturing (e.g., during shipping and/or before implantation into a patient), device 100 may operate in shelf mode 1402. As described previously, shelf mode 1402 may be a lower power operating mode in which device 100 ignores toggling sequences between the presence and the absence of externally-generated static magnet fields, but from which device 100 may periodically (e.g., for a first amount of time once every period of a second amount of time at least ten times larger than the first amount of time) automatically and temporarily switch to a waking operating mode (not explicitly shown in FIG. 14) in which device 100 attempts to detect an initial toggling sequence. While in the waking operating mode associated with shelf mode 1402, if device 100 detects the initial toggling sequence and further detects that the access code is encoded within the initial toggling sequence as described above, device 100 may transition from shelf mode 1402 to manual session mode 1408, as illustrated by transition 1412. If device 100 does not detect the access code for a time, device 100 remains in shelf mode, continuing to ignore toggling sequences most of the time and periodically waking to attempt to detect an initial toggling sequence with a valid access code.

In manual session mode 1408, a therapy session (e.g., an electroacupuncture stimulation session) may be performed. Because manual session mode 1408 may be transitioned to in response to receiving commands from external controller 800 (e.g., by receiving the access code while in shelf mode 1402 as described above, etc.), the session is considered to be a "manual" session (i.e., that is performed on demand), rather than an "automatic" session (i.e., that is performed without human intervention at a scheduled time). If the manual session completes, manual session mode 1408 may automatically transition to sleep mode 1404, as illustrated by transition 1414. In other examples, a user may not wish to wait for the manual session to finish before going into sleep mode 1404. As such, a STOP command (e.g., triggered by the STOP button on external controller 800) may cause device 100 to transition to sleep mode 1404 prior to completion of the manual session, as illustrated by transition 1416.

Sleep mode 1404 may be a similar low power mode like shelf mode 1402 described above. However, a major difference between shelf mode 1402 and sleep mode 1404 is that automatic sessions (e.g., scheduled stimulation sessions according to a stimulation regimen such as described above for EA device 200) may be performed at scheduled times. For example, as shown, when the scheduled time for a stimulation session arrives, device 100 may automatically transition to automatic session mode 1406, as illustrated by transition 1418. In automatic session mode 1406, stimulation may be applied according to settings (e.g., amplitudes, durations, etc.) previously configured in device 100. However, as illustrated, device 100 may not be controllable (i.e., may ignore toggling sequences) while in automatic session mode 1406 while the automatic session is ongoing. Only when the automatic session has completed (i.e., timed out) does device 100 automatically transition back to sleep mode 1404, as illustrated by transition 1420. Sleep mode may be the mode that device 100 operates in the large majority of the time after being implanted in the patient.

As described above in relation to shelf mode 1402 (and in contrast to automatic session mode 1406), device 100 may transition from sleep mode 1404 to manual session mode 1408 if an initial toggling sequence is detected in which a valid access code is provided. Sleep mode 1404 may automatically transition to a waking operating mode (not explicitly shown) periodically to briefly check for such an initial toggling sequence in the same way described above for shelf mode 1402. The transition to manual session mode 1408 triggered by receiving the access code is illustrated by transition 1422.

While in manual session mode 1408, device 100 may be controllable by external controller 800. In other words, device 100 may detect, rather than ignore, toggling sequences, identify multi-bit commands encoded within digital data streams represented by the toggling sequences, and perform actions associated with the multi-bit commands, as described above. As one example, device 100 may accept multi-bit commands to increase or decrease a parameter (e.g., a stimulation amplitude level, duration, etc.) for the manual sessions and/or for future automatic sessions, and/or to configure one or more other device settings. As illustrated by transition 1424, device 100 may remain in manual session mode while such commands are transmitted and such actions are performed. Additionally, while in manual session mode 1408, device 100 may receive a command to turn OFF (i.e., to return to shelf mode 1402 rather than sleep mode 1404 such that further automatic sessions will not be performed). The action associated with a multi-bit command to turn OFF may be to transition to shelf mode 1402, as illustrated by transition 1426.

In other examples while in manual session mode 1408, device 100 may receive a command to accept advanced commands. For example, while basic commands may include a relatively small number of bits (e.g., four bits) in order to allow the basic commands to be transmitted relatively quickly and conveniently, it may be desirable for device 100 to listen for (i.e., buffer and detect) longer, less common, and/or more sophisticated commands (e.g., twelve bit commands). Because the basic command space (e.g., a four-bit command space in which each command has a distinct minimum form) may not include sufficient bits to represent more than a small number of basic commands, a larger command space (e.g., a twelve-bit command space in which each command has a distinct minimum form) may be used to encode a larger number of advanced commands. As illustrated by transition 1428, device 100 may transition to advanced command mode 1410 based on receiving a command to do so while in manual session mode 1408. Additionally, as illustrated by transition 1430, device 100 may return from advanced command mode 1410 to manual session mode 1408 based on the same or another command (e.g., after receiving and performing advanced commands while in advanced command mode 1410).

Figure 15:
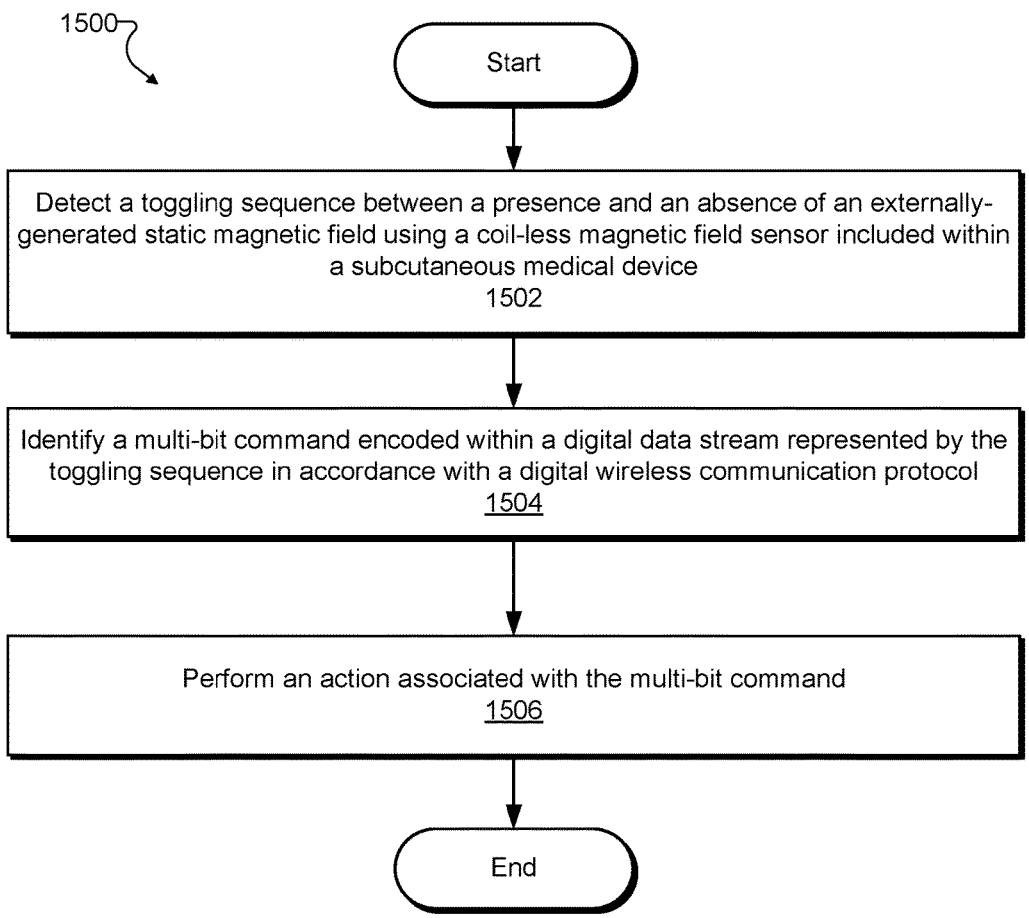
FIGS. 15 and 16 illustrate exemplary methods of wireless communication with a subcutaneous medical device according to principles described herein.

FIG. 15 illustrates an exemplary method 1500 of wireless communication with a subcutaneous medical device such as device 100. While FIG. 15 illustrates exemplary operations according to one embodiment, other embodiments may omit, add to, reorder, and/or modify any of the operations shown in FIG. 15. One or more of the operations shown in FIG. 15 may be performed by device 100 and/or any implementation thereof (e.g., EA device 200).

In operation 1502, a subcutaneous medical device implanted within a patient and using a coil-less magnetic field sensor included within the subcutaneous medical device may detect a toggling sequence between a presence and an absence of an externally-generated static magnetic field. For example, the toggling sequence may be representative of a digital data stream according to a digital wireless communication protocol. Operation 1502 may be performed in any of the ways described herein.

In operation 1504 the subcutaneous medical device may identify a multi-bit command encoded within the digital data stream represented by the toggling sequence. Operation 1504 may be performed in any of the ways described herein. For example, the subcutaneous medical device may identify the multi-bit command based on the detected toggling sequence and in accordance with the digital wireless communication protocol.

In operation 1506 the subcutaneous medical device may perform an action associated with the multi-bit command. Operation 1506 may be performed in any of the ways described herein. For example, the subcutaneous medical device may perform the action in response to the identifying of the multi-bit command.

Figure 16:
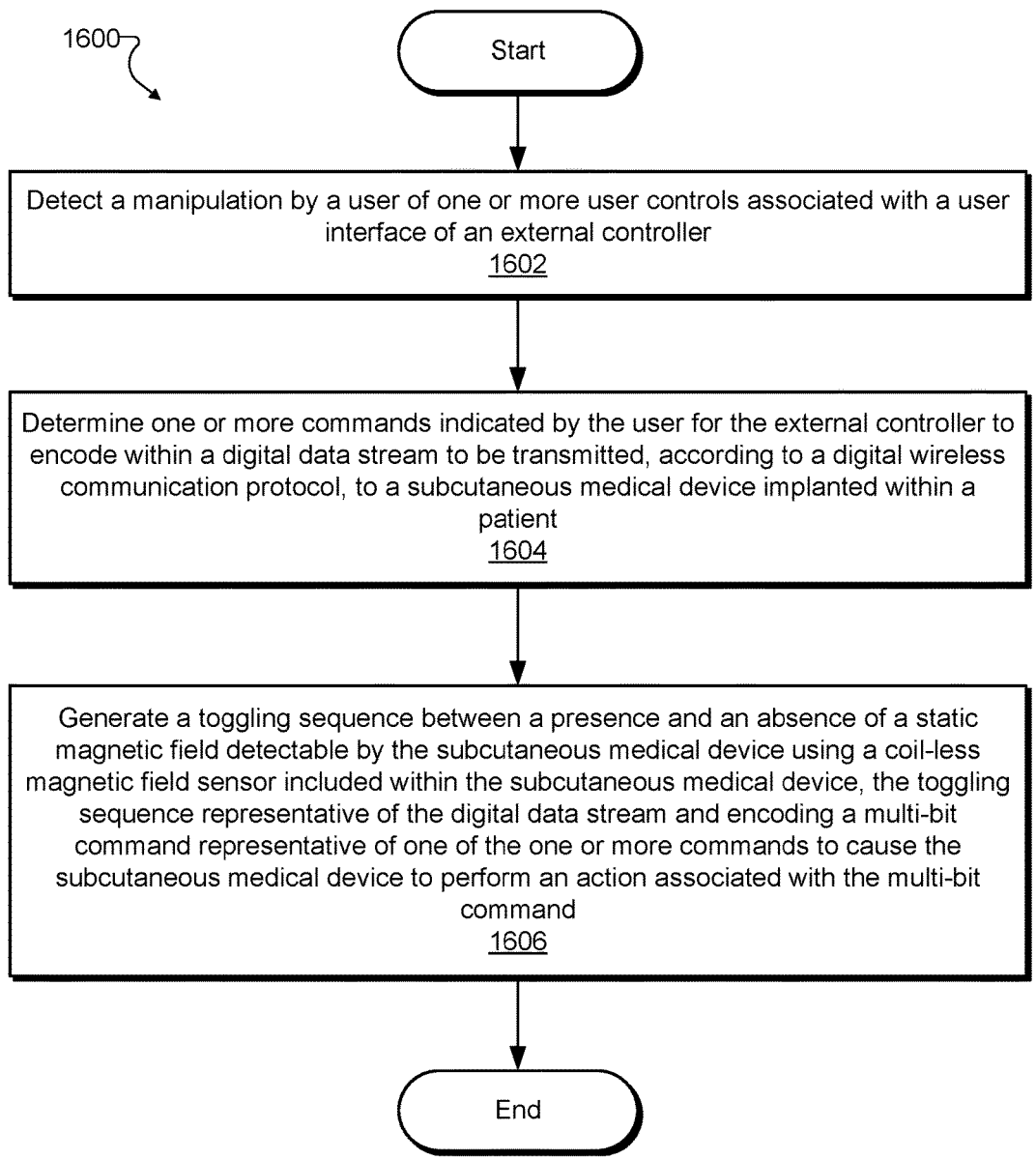

FIG. 16 illustrates an exemplary method 1600 of wireless communication with a subcutaneous medical device such as device 100. While FIG. 16 illustrates exemplary operations according to one embodiment, other embodiments may omit, add to, reorder, and/or modify any of the operations shown in FIG. 16. One or more of the operations shown in FIG. 16 may be performed by external controller 800 and/or any implementation thereof.

In operation 1602, an external controller located near a patient at a site where a subcutaneous medical device is implanted within the patient may detect a manipulation by a user of one or more user controls associated with a user interface of the external controller. Operation 1602 may be performed in any of the ways described herein.

In operation 1604 the external controller may determine one or more commands indicated by the user for the external controller to encode within a digital data stream to be transmitted to the subcutaneous medical device according to a digital wireless communication protocol. Operation 1604 may be performed in any of the ways described herein. For example, the external controller may determine the one or more commands based on the detecting of the manipulation of the one or more user controls in operation 1602.

In operation 1606 the external controller may generate a toggling sequence between a presence and an absence of a static magnetic field detectable by the subcutaneous medical device using a coil-less magnetic field sensor included within the subcutaneous medical device. For example, the toggling sequence may be representative of the digital data stream and may encode a multi-bit command representative of one of the one or more commands. As such, when the generated toggling sequence is identified by the subcutaneous medical device, the subcutaneous medical device may perform an action associated with the multi-bit command. Operation 1606 may be performed in any of the ways described herein. For example, the external controller may generate the toggling sequence based on the determining of the one or more commands in operation 1604. Additionally, the external controller may generate the toggling sequence using an electromagnet within the external controller that creates the presence of the static magnetic field when the electromagnet is energized and creates the absence of the static magnetic field when the electromagnet is de-energized.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    detecting, by a subcutaneous medical device implanted within a patient and using a coil-less magnetic field sensor included within the subcutaneous medical device, a toggling sequence between a presence and an absence of an externally-generated static magnetic field, the toggling sequence representative of a digital data stream according to a digital wireless communication protocol that specifies
        as a first binary value, a first range for a duration between changes to the externally-generated static magnetic field in the toggling sequence, and
        as a second binary value, a second range for the duration between the changes to the externally-generated static magnetic field in the toggling sequence;
    identifying, by the subcutaneous medical device based on the detected toggling sequence and in accordance with the digital wireless communication protocol, a multi-bit command encoded within the digital data stream represented by the toggling sequence; and
    performing, by the subcutaneous medical device in response to the identifying of the multi-bit command, an action associated with the multi-bit command.

2. The method of claim 1, wherein:
    the subcutaneous medical device is a subcutaneous neuromodulation system including an electroacupuncture device implanted beneath a skin surface of the patient at an acupoint, the electroacupuncture device having an electrode configuration thereon that is configured to deliver stimulation pulses to tissue of the patient at the acupoint in accordance with a stimulation regimen and that includes
        a central electrode of a first polarity centrally located on a surface of a housing of the electroacupuncture device, and
        an annular electrode of a second polarity and that is spaced apart from the central electrode; and
    the stimulation regimen includes a plurality of stimulation sessions in which the tissue of the patient at the acupoint is stimulated, the stimulation sessions each having a duration of T3 minutes and occurring at a rate of once every T4 minutes such that a duty cycle of the stimulation sessions is a ratio of T3 to T4 and is less than 0.05.

3. The method of claim 1, wherein:
    the first binary value is a binary zero and the first range for the duration between the changes to the externally-generated static magnetic field is a range from zero milliseconds up to a first number of milliseconds; and
    the second binary value is a binary one and the second range for the duration between the changes to the externally-generated static magnetic field is a range from the first number of milliseconds up to a second number of milliseconds, the second number of milliseconds greater than the first number of milliseconds.

4. The method of claim 3, wherein:
    the subcutaneous medical device captures one or more instances of the binary zero and of the binary one included within the digital data stream represented by the toggling sequence using a first-in-first-out ("FIFO") buffer; and
    the digital wireless communication protocol specifies, as a reset value to clear the FIFO buffer, a third range for the duration between the changes to the externally-generated static magnetic field in the toggling sequence that is a range from the second number of milliseconds to an unlimited number of milliseconds.

5. The method of claim 4, further comprising:
    detecting, by the subcutaneous medical device subsequent to the identifying of the multi-bit command and based on the detected toggling sequence, the reset value to clear the FIFO buffer;
    clearing, by the subcutaneous medical device in response to the detected reset value, the FIFO buffer;
    identifying, by the subcutaneous medical device based on additional binary values represented in the toggling sequence subsequent to the reset value, an additional multi-bit command encoded within the digital data stream and different from the multi-bit command; and
    performing, by the subcutaneous medical device in response to the identifying of the additional multi-bit command and subsequent to the performing of the action associated with the multi-bit command, an additional action associated with the additional multi-bit command.

6. The method of claim 4, wherein:
    the digital wireless communication protocol specifies a period lasting a particular amount of time in which the digital data stream contains only one multi-bit command;
    the multi-bit command encoded within the digital data stream is repeated within the digital data stream at least once within the period; and
    the identifying of the multi-bit command includes determining the commencement of each repeated instance of the multi-bit command by at least one of
        detecting, within the toggling sequence prior to each repeated instance of the multi-bit command, the reset value to clear the FIFO buffer, and
        converting a plurality of bits representative of the multi-bit command and captured using the FIFO buffer into a minimum form.

7. The method of claim 1, wherein the action associated with the multi-bit command is to switch from one operating mode in a plurality of operating modes in which the subcutaneous medical device may operate to another operating mode in the plurality of operating modes, the plurality of operating modes including a shelf mode, a sleep mode, an automatic session mode, and a manual session mode.

8. The method of claim 7, wherein:
the digital wireless communication protocol specifies one or more basic multi-bit commands each defined by a first number of bits and further specifies one or more advanced multi-bit commands each defined by a second number of bits greater than the first number of bits; and
the plurality of operating modes includes an advanced command mode in which the identifying of the multi-bit command includes identifying an advanced multi-bit command from the one or more advanced multi-bit commands defined by the second number of bits.

9. The method of claim 1, further comprising:
detecting, by the subcutaneous medical device using the coil-less magnetic field sensor, an initial toggling sequence between the presence and the absence of the externally-generated static magnetic field, the initial toggling sequence representative of an initial digital data stream according to the digital wireless communication protocol;
determining, by the subcutaneous medical device based on the detected initial toggling sequence and in accordance with the digital wireless communication protocol, that a predetermined access code is encoded within the initial digital data stream represented by the initial toggling sequence; and
allowing, by the subcutaneous medical device in response to the determining that the predetermined access code is encoded within the initial digital data stream, access control to the subcutaneous medical device such that the detecting of the toggling sequence representative of the digital data stream in which the multi-bit command is encoded is performed in response to the allowing of the access control.

10. The method of claim 1, further comprising:
operating, by the subcutaneous medical device, in a low power operating mode in which the subcutaneous medical device ignores toggling sequences between the presence and the absence of the externally-generated static magnetic field; and
automatically and temporarily switching, by the subcutaneous medical device for a first amount of time once every period of a second amount of time, from operating in the low power operating mode in which the subcutaneous medical device ignores the toggling sequences to a waking operating mode in which the detecting of the initial toggling sequence is performed, the second amount of time at least ten times larger than the first amount of time.

11. The method of claim 1, wherein the toggling sequence between the presence and the absence of the externally-generated static magnetic field is generated by an external controller when the external controller is located near the patient at a site where the subcutaneous medical device is implanted, the external controller including:
a user interface including one or more user controls manipulable by a user of the external controller to indicate one or more commands for the external controller to encode within the digital data stream transmitted to the subcutaneous medical device; and
an electromagnet configured to be energized and de-energized in accordance with the digital wireless communication protocol to implement the toggling sequence representative of the digital data stream transmitted to the subcutaneous medical device and in which the one or more commands indicated by the user including the multi-bit command are encoded.

12. The method of claim 11, further comprising indicating, by the subcutaneous medical device in response to at least one of the identifying of the multi-bit command and the performing of the action associated with the multi-bit command, at least one of an acknowledgment (ACK) response and a non-acknowledgement (NACK) response configured to be detected by the external controller.

13. The method of claim 1, wherein the coil-less magnetic field sensor is at least one of an anisotropic magnetoresistance (AMR) sensor, a Hall effect sensor, and a Reed switch.

14. A method comprising:
detecting, by an external controller located near a patient at a site where a subcutaneous medical device is implanted within the patient, a manipulation by a user of one or more user controls associated with a user interface of the external controller;
determining, by the external controller based on the detecting of the manipulation of the one or more user controls, one or more commands indicated by the user for the external controller to encode within a digital data stream to be transmitted to the subcutaneous medical device according to a digital wireless communication protocol that specifies
as a first binary value, a first range for a duration between changes to the externally-generated static magnetic field in the toggling sequence, and
as a second binary value, a second range for the duration between the changes to the externally-generated static magnetic field in the toggling sequence; and
generating, by the external controller based on the determining of the one or more commands, a toggling sequence between a presence and an absence of a static magnetic field detectable by the subcutaneous medical device using a coil-less, magnetic field sensor included within the subcutaneous medical device, the toggling sequence representative of the digital data stream and encoding a multi-bit command representative of one of the one or more commands and that, when identified by the subcutaneous medical device, causes the subcutaneous medical device to perform an action associated with the multi-bit command;
wherein the toggling sequence is generated using an electromagnet within the external controller that creates the presence of the static magnetic field when the electromagnet is energized and the absence of the static magnetic field when the electromagnet is de-energized.

15. The method of claim 14, wherein:
the subcutaneous medical device is a subcutaneous neuromodulation system including an electroacupuncture device implanted beneath a skin surface of the patient at an acupoint, the electroacupuncture device having an electrode configuration thereon that is configured to deliver stimulation pulses to tissue of the patient at the acupoint in accordance with a stimulation regimen and that includes
a central electrode of a first polarity centrally located on a surface of a housing of the electroacupuncture device, and an annular electrode of a second polarity and that is spaced apart from the central electrode; and the stimulation regimen includes a plurality of stimulation sessions in which the tissue of the patient at the acupoint is stimulated, the stimulation sessions each having a duration of T3 minutes and occurring at a rate of once every T4 minutes such that a duty cycle of the stimulation sessions is a ratio of T3 to T4 and is less than 0.05.

16. A subcutaneous medical device for implantation within a patient, the subcutaneous medical device comprising:

a coil-less magnetic field sensor that detects a toggling sequence between a presence and an absence of an externally-generated static magnetic field, the toggling sequence representative of a digital data stream according to a digital wireless communication protocol that specifies as a first binary value, a first range for a duration between changes to the externally-generated static magnetic field in the toggling sequence, and as a second binary value, a second range for the duration between the changes to the externally-generated static magnetic field in the toggling sequence; and control circuitry communicatively coupled with the coil-less magnetic field sensor and that identifies, based on the detected toggling sequence and in accordance with the digital wireless communication protocol, a multi-bit command encoded within the digital data stream represented by the toggling sequence, and performs, in response to the identification of the multi-bit command, an action associated with the multi-bit command.

17. The subcutaneous medical device of claim 16, wherein:

the subcutaneous medical device is a subcutaneous neuromodulation system including an electroacupuncture device implanted beneath a skin surface of the patient at an acupoint, the electroacupuncture device having an electrode configuration thereon that is configured to deliver stimulation pulses to tissue of the patient at the acupoint in accordance with a stimulation regimen and that includes a central electrode of a first polarity centrally located on a surface of a housing of the electroacupuncture device, and an annular electrode of a second polarity and that is spaced apart from the central electrode; and the stimulation regimen includes a plurality of stimulation sessions in which the tissue of the patient at the acupoint is stimulated, the stimulation sessions each having a duration of T3 minutes and occurring at a rate of once every T4 minutes such that a duty cycle of the stimulation sessions is a ratio of T3 to T4 and is less than 0.05.

18. The subcutaneous medical device of claim 16, wherein:

the first binary value is a binary zero and the first range for the duration between the changes to the externally-generated static magnetic field is a range from zero milliseconds up to a first number of milliseconds; and the second binary value is a binary one and the second range for the duration between the changes to the externally-generated static magnetic field is a range from the first number of milliseconds up to a second number of milliseconds, the second number of milliseconds greater than the first number of milliseconds.

19. The subcutaneous medical device of claim 18, wherein:

the subcutaneous medical device captures one or more instances of the binary zero and of the binary one included within the digital data stream represented by the toggling sequence using a first-in-first-out ("FIFO") buffer; and the digital wireless communication protocol specifies, as a reset value to clear the FIFO buffer, a third range for the duration between the changes to the externally-generated static magnetic field in the toggling sequence that is a range from the second number of milliseconds to an unlimited number of milliseconds.

20. The subcutaneous medical device of claim 16, wherein the control circuitry further:

detects, using the coil-less magnetic field sensor, an initial toggling sequence between the presence and the absence of the externally-generated static magnetic field, the initial toggling sequence representative of an initial digital data stream according to the digital wireless communication protocol;

determines, based on the detected initial toggling sequence and in accordance with the digital wireless communication protocol, that a predetermined access code is encoded within the initial digital data stream represented by the initial toggling sequence; and allows, in response to the determining that the predetermined access code is encoded within the initial digital data stream, access control to the subcutaneous medical device such that the detecting of the toggling sequence representative of the digital data stream in which the multi-bit command is encoded is performed in response to the allowing of the access control.

* * * * *